US010671155B2

(12) United States Patent
Dziuk et al.

(10) Patent No.: US 10,671,155 B2
(45) Date of Patent: Jun. 2, 2020

(54) MULTI-TRACK PLAYBACK OF MEDIA CONTENT DURING REPETITIVE MOTION ACTIVITIES

(71) Applicant: Spotify AB, Stockholm (SE)

(72) Inventors: Dariusz Dziuk, Stockholm (SE); Rahul Sen, Stockholm (SE)

(73) Assignee: SPOTIFY AB, Stockholm (SE)

( * ) Notice: Subject to any disclaimer, the term of this patent is extended or adjusted under 35 U.S.C. 154(b) by 0 days.

(21) Appl. No.: 16/279,957

(22) Filed: Feb. 19, 2019

(65) Prior Publication Data

US 2019/0220084 A1 Jul. 18, 2019

Related U.S. Application Data

(63) Continuation of application No. 15/269,864, filed on Sep. 19, 2016, now Pat. No. 10,248,190, which is a
(Continued)

(51) Int. Cl.
*G06F 3/01* (2006.01)
*A61B 5/024* (2006.01)
(Continued)

(52) U.S. Cl.
CPC .............. *G06F 3/011* (2013.01); *A61B 5/024* (2013.01); *A63B 71/00* (2013.01); *G06F 3/0482* (2013.01);
(Continued)

(58) Field of Classification Search
CPC . G06F 3/01; G06F 3/011; G06F 3/162; G06F 3/165; G06F 3/167; G06F 3/017;
(Continued)

(56) References Cited

U.S. PATENT DOCUMENTS

| 5,212,733 A | 5/1993 | DeVitt et al. |
| 5,812,688 A | 9/1998 | Gibson |

(Continued)

FOREIGN PATENT DOCUMENTS

| EP | 2045704 A2 | 8/2009 |
| EP | 2226715 A2 | 9/2010 |

(Continued)

OTHER PUBLICATIONS

Android Police, "Hands—On With Samsung Milk: Music Made Refreshingly Simple . . . And Creamy", http://www.androidpolice.com/2014/03/07/hands—0n-with-samsung-milk-music-made-refreshingly-simple-and-creamy-video/, 6 pages, published on Mar. 7, 2014. (Downloaded on Sep. 26, 2016.).

(Continued)

*Primary Examiner* — Andrew C Flanders
(74) *Attorney, Agent, or Firm* — Merchant & Gould P.C.

(57) ABSTRACT

A system for multi-track playback of media content includes: a media device; a user interface, provided at the media device, which displays a visual array of media options, a playback logic, provided within the media device, which is configured so that, while a selected point or region is determined by the user interface as being moved in response to user input, within the visual array of media options, the system determines media options that are proximate to the selected point or region, and adjusts playback parameters for corresponding media content items, by crossfading or otherwise combining playback to reflect the media options relative distances from the selected point or region; and a tempo logic, provided within the media device, which is configured to provide or receive a selected tempo and provide the one or more media content items associated with the selected tempo.

12 Claims, 18 Drawing Sheets

Related U.S. Application Data continuation of application No. 14/883,273, filed on Oct. 14, 2015, now Pat. No. 9,606,620.

(60) Provisional application No. 62/163,887, filed on May 19, 2015.

(51) Int. Cl.

| | | |
|---|---|---|
| G06F 3/16 | (2006.01) | |
| G06F 3/0482 | (2013.01) | |
| G06F 3/0484 | (2013.01) | |
| G11B 27/038 | (2006.01) | |
| G11B 27/10 | (2006.01) | |
| G11B 27/34 | (2006.01) | |
| A63B 71/00 | (2006.01) | |

(52) U.S. Cl.
CPC .......... *G06F 3/04847* (2013.01); *G06F 3/165* (2013.01); *G11B 27/038* (2013.01); *G11B 27/105* (2013.01); *G11B 27/34* (2013.01); *A63B 2230/062* (2013.01)

(58) Field of Classification Search
CPC .. G06F 3/0488; G06F 3/04847; G06F 3/0482; G06F 1/1692; G06F 3/16; G06F 3/0485; G06F 3/0486; G11B 27/038; H04S 7/30; H04S 3/002; H04S 1/002; H04S 2420/01; G10H 2220/106; G10H 2220/111; G10H 2220/116; G10H 2220/131; A61B 5/024; A63B 2230/062

See application file for complete search history.

(56) References Cited

U.S. PATENT DOCUMENTS

| | | | |
|---|---|---|---|
| 6,005,563 A | 12/1999 | White et al. | |
| 6,490,359 B1 | 12/2002 | Gibson | |
| 6,654,367 B1 | 11/2003 | Kaufman | |
| 6,976,215 B1 | 12/2005 | Roderick et al. | |
| 7,571,014 B1 | 8/2009 | Lambourne et al. | |
| 7,742,609 B2 | 6/2010 | Yeakel et al. | |
| 8,073,160 B1 | 12/2011 | Classen | |
| 9,423,998 B2 | 8/2016 | Dziuk | |
| 9,449,109 B1 | 9/2016 | Keel et al. | |
| 9,606,620 B2 | 3/2017 | Dziuk et al. | |
| 2001/0030660 A1 | 10/2001 | Zainoulline | |
| 2002/0103919 A1 | 8/2002 | Hannaway | |
| 2002/0120752 A1 | 8/2002 | Logan et al. | |
| 2003/0126605 A1 | 7/2003 | Betz et al. | |
| 2004/0056885 A1 | 3/2004 | Azami et al. | |
| 2004/0268413 A1 | 12/2004 | Reid et al. | |
| 2005/0071747 A1* | 3/2005 | Jaeger | G06F 3/04883 715/200 |
| 2005/0275626 A1 | 12/2005 | Mueller et al. | |
| 2006/0107822 A1* | 5/2006 | Bowen | G10H 1/0008 84/612 |
| 2006/0117261 A1 | 6/2006 | Sim et al. | |
| 2006/0152622 A1 | 7/2006 | Tran et al. | |
| 2006/0259877 A1 | 11/2006 | Kaminagayoshi | |
| 2006/0265349 A1 | 11/2006 | Hicken | |
| 2007/0130159 A1 | 6/2007 | Gulli et al. | |
| 2007/0180979 A1 | 8/2007 | Rosenberg | |
| 2007/0192739 A1 | 8/2007 | Hunleth et al. | |
| 2007/0222768 A1 | 9/2007 | Geurts et al. | |
| 2007/0227337 A1* | 10/2007 | Yoshikawa | G10H 1/0025 84/602 |
| 2008/0026690 A1 | 1/2008 | Foxenland | |
| 2008/0086687 A1 | 4/2008 | Sakai et al. | |
| 2008/0255688 A1 | 10/2008 | Castel et al. | |
| 2009/0019398 A1 | 1/2009 | Hansson et al. | |
| 2009/0043410 A1 | 2/2009 | Evans et al. | |
| 2009/0046545 A1 | 2/2009 | Blinnikka | |
| 2009/0158198 A1 | 6/2009 | Hayter et al. | |
| 2009/0193465 A1 | 7/2009 | Yi | |
| 2009/0316913 A1 | 12/2009 | McGrath | |
| 2010/0053192 A1 | 3/2010 | Miyazaki | |
| 2010/0229094 A1 | 9/2010 | Nakajima et al. | |
| 2010/0262938 A1 | 10/2010 | Woods et al. | |
| 2010/0302445 A1 | 12/2010 | Kunihara | |
| 2011/0035705 A1* | 2/2011 | Faenger | G06F 16/4387 715/811 |
| 2011/0061028 A1* | 3/2011 | Bachman | G06F 3/0482 715/862 |
| 2011/0234480 A1 | 9/2011 | Fino et al. | |
| 2012/0015729 A1 | 1/2012 | Takehiro | |
| 2012/0042007 A1 | 2/2012 | Weel | |
| 2012/0066186 A1* | 3/2012 | Wohlert | G11B 27/034 707/691 |
| 2012/0078398 A1 | 3/2012 | Xu et al. | |
| 2012/0109348 A1* | 5/2012 | Matsunaga | G06F 3/04847 700/94 |
| 2012/0173981 A1 | 7/2012 | Day | |
| 2012/0311444 A1 | 12/2012 | Chaudhri | |
| 2013/0047084 A1 | 2/2013 | Sanders et al. | |
| 2013/0067328 A1 | 3/2013 | Salyards et al. | |
| 2013/0113737 A1 | 5/2013 | Shiba | |
| 2013/0178962 A1 | 7/2013 | DiMaria et al. | |
| 2014/0035831 A1 | 2/2014 | Fino | |
| 2014/0108929 A1 | 4/2014 | Garmark et al. | |
| 2014/0115114 A1 | 4/2014 | Garmark et al. | |
| 2014/0115468 A1 | 4/2014 | Guerrero | |
| 2014/0122589 A1 | 5/2014 | Fyke et al. | |
| 2014/0123006 A1 | 5/2014 | Chen et al. | |
| 2014/0181199 A1 | 6/2014 | Kumar et al. | |
| 2014/0181656 A1 | 6/2014 | Kumar et al. | |
| 2014/0215334 A1 | 7/2014 | Garmark et al. | |
| 2014/0223303 A1 | 8/2014 | Cox et al. | |
| 2014/0304756 A1 | 10/2014 | Fletcher | |
| 2014/0306976 A1 | 10/2014 | Sugiura et al. | |
| 2014/0325357 A1 | 10/2014 | Sant et al. | |
| 2014/0331133 A1 | 11/2014 | Coburn, IV et al. | |
| 2015/0002046 A1 | 1/2015 | Schlangen | |
| 2015/0205864 A1 | 7/2015 | Fuzell-Casey et al. | |
| 2015/0234564 A1 | 8/2015 | Snibbe et al. | |
| 2015/0277707 A1 | 10/2015 | Dziuk et al. | |
| 2015/0334204 A1 | 11/2015 | Bilinski et al. | |
| 2016/0035323 A1 | 2/2016 | Na et al. | |
| 2016/0054913 A1 | 2/2016 | Snibbe et al. | |
| 2016/0103589 A1 | 4/2016 | Dziuk | |
| 2016/0103595 A1 | 4/2016 | Dziuk et al. | |
| 2016/0103656 A1 | 4/2016 | Dziuk | |

FOREIGN PATENT DOCUMENTS

| | | |
|---|---|---|
| EP | 2320335 A2 | 5/2011 |
| EP | 2434491 A1 | 3/2012 |
| EP | 2925008 A1 | 9/2015 |
| EP | 3059973 A1 | 8/2016 |
| WO | 2015/154515 A1 | 10/2015 |

OTHER PUBLICATIONS

Android Static, "Milk Music: A New Ad-Free Streaming Music App from Samsung", http://www.androidstatic.com/milk-music-new-ad-free-streaming-music-app-samsung/, 5 pages, published on Mar. 7, 2014. (Downloaded on Sep. 26, 2016.).

Anonymous: "user interface—How does the algorithm to color the song list in iTunes 11 work?—Stack Overflow", May 10, 2013 (May 10, 2013), XP055363994, Retrieved from the Internet: URL:http://stackoverflow.com/questions/13637892/how-does-the-algorithm-to-color-the-song-list-in-itunes-11-work?answertab=oldest#tab-top [retrieved on Apr. 11, 2017].

CNET, "Hands on with Samsung's Milk Music", http://www.cnet.com/products/milk-android/preview/, 5 pages, published on Mar. 6, 2014. (Downloaded on Sep. 26, 2016.).

U.S. Appl. No. 14/883,232, filed Oct. 14, 2015 for "Cadence Determination and Media Content Selection".

U.S. Appl. No. 14/883,245, filed Oct. 14, 2015 for "Heart Rate Control Based Upon Media Content Selection".

(56) References Cited

OTHER PUBLICATIONS

U.S. Appl. No. 14/883,252, filed Oct. 14, 2015 for "Repetitive Motion Activity Enhancement Based Upon Media Content Selection".
U.S. Appl. No. 14/883,295, filed Oct. 14, 2015 for "Search Media Content Based Upon Tempo".
U.S. Appl. No. 14/883,298, filed Oct. 14, 2015 for "Cadence-Based Playlists Management System".
U.S. Appl. No. 14/883,318, filed Oct. 14, 2015 for "Cadence and Media Content Phase Alignment".
U.S. Appl. No. 14/883,323, filed Oct. 14, 2015 for "Accessibility Management System for Media Content Items".
U.S. Appl. No. 14/883,336, filed Oct. 14, 2015 for "Selection and Playback of Song Versions Using Cadence".
U.S. Appl. No. 14/883,340, filed Oct. 14, 2015 for "Cadence-Based Selection, Playback, and Transition Between Song Versions".
U.S. Appl. No. 14/944,972, filed Nov. 18, 2015 for "System for Managing Transitions Between Media Content Items".
U.S. Appl. No. 14/945,008, filed Nov. 18, 2015 for "Identifying Media Content".
Extended European Search Report and Written Opinion for European Patent Application No. 14162386.8, dated Aug. 25, 2014.
Extended European Search Report for Application No. 16199679.8, dated Feb. 13, 2017.
Extended European Search Report for European Patent Application No. 16161961.4, dated Jun. 15, 2016.
Final Office Action from the United States Patent and Trademark Office for U.S. Appl. No. 14/231,170, dated Oct. 28, 2014, 28 pages.
Final Office Action from the United States Patent and Trademark Office for U.S. Appl. No. 14/231,203, dated Oct. 28, 2014, 15 pages.
International Preliminary Report on Patentability for PCT Application No. PCT/EP2017/055369, completed May 24, 2018.
International Preliminary Report on Patentability issued in International Application No. PCT/182013/002808 dated Apr. 14, 2015, 16 pages.
International Search Report and Written Opinion from International Patent Application No. PCT/EP2017/055369, dated Apr. 24, 2017.
Notice of Allowance from the United States Patent and Trademark office for U.S. Appl. No. 14/879,737, dated Apr. 12, 2016, 9 pages.
Notice of Allowance from the United States Patent and Trademark office for U.S. Appl. No. 14/879,743, dated Jun. 20, 2016, 8 pages.
Notice of Allowance from the United States Patent and Trademark office for U.S. Appl. No. 14/879,774, dated Jul. 6, 2016, 7 pages.
Office Action from the United States Patent and Trademark Office for U.S. Appl. No. 15/263,084, dated Apr. 19, 2018, 19 pages.
Office Action from the United States Patent and Trademark Office for U.S. Appl. No. 14/053,443, dated Apr. 27, 2015, 11 pages.
Office Action from the United States Patent and Trademark Office for U.S. Appl. No. 14/060,495, dated Jul. 27, 2015, 18 pages.
Office Action from the United States Patent and Trademark Office for U.S. Appl. No. 14/231,170, dated Jun. 26, 2014, 22 pages.
Office Action from the United States Patent and Trademark Office for U.S. Appl. No. 14/231,170, dated May 7, 2015, 29 pages.
Office Action from the United States Patent and Trademark Office for U.S. Appl. No. 14/231,203, dated Jun. 18, 2014, 12 pages.
Office Action from the United States Patent and Trademark Office for U.S. Appl. No. 14/231,203, dated May 13, 2015, 16 pages.
Office Action from the United States Patent and Trademark Office for U.S. Appl. No. 14/231,203, dated Sep. 17, 2015, 16 pages.
Office Action from the United States Patent and Trademark Office for U.S. Appl. No. 14/879,743, dated Mar. 1, 2016, 8 pages.
Office Action from the United States Patent and Trademark Office for U.S. Appl. No. 14/879,774, dated Feb. 8, 2016, 11 pages.
Office Action from U.S. Appl. No. 15/065,735, dated Oct. 28, 2016, 28 pages.
"Samsung Introduces Milk Music, the Next Big Thing in Music", https://news.samsung.com/global/samsung-introducesmilk-music-the-next-big-thing-in-music, 4 pages, published on Mar. 8, 2014. (Downloaded on Sep. 26, 2016.).
"Samsung Milk Music Design Story—Unexpected Music Discovery", http://www.design.samsung.com/global/contents/milk_music/, 3 pages, published Mar. 2014. (Downloaded on Sep. 26, 2016.).
Summons to attend oral proceedings pursuant to Rule 115(1) EPC issued on European patent application No. 14162386.8, dated Nov. 25, 2015, 12 pages.
The Verge, "Samsung takes another crack at streaming radio with Milk", http://www.theverge.com/2014/3/7/5481482/samsung-takes-another-crack-at-streaming-radio-with-milk, 18 pages, published on Mar. 7, 2014. (Downloaded on Sep. 26, 2016.).
Communication Pursuant to Article 94(3) EPC issued in European Application No. 16170279.0, dated Apr. 9, 2019.
Anonymous: "PaceDJ can help you create the perfect workout mix", PCWorld, Jul. 30, 2012. Retrieved from the Internet: https://www.pcworld.com/article/2000246/pacedj-can-help-you-create-the-perfect-workout-mix.html [retrieved on Apr. 2, 2019].

* cited by examiner

MULTI-TRACK PLAYBACK OF MEDIA CONTENT DURING REPETITIVE MOTION ACTIVITIES

RELATED APPLICATIONS

This application is a Continuation of U.S. Ser. No. 15/269,864, filed Sep. 19, 2016, which is a Continuation of U.S. Ser. No. 14/883,273, filed Oct. 14, 2015, which claims priority to U.S. Ser. No. 62/163,887, filed on May 19, 2015, and is related to U.S. Ser. No. 14/228,605, the disclosures of which are hereby incorporated by reference in their entireties. To the extent appropriate, a claim of priority is made to each of the above-disclosed applications.

BACKGROUND

The digital media industry has evolved greatly within the past several years. Today's consumers enjoy the ability to access a tremendous amount of media content, such as music and videos, at any location or time of day, using a wide variety of computing systems, handheld entertainment devices, smartphones, or other types of media device. With the availability of reliable high-speed Internet connectivity, and advances in digital rights management, many users can now stream media content, on demand, from peer devices or remote servers.

However, with the increase in the amount of media content available, there exists the challenge of how to best provide access to that content. For example, users generally prefer to interact with media content libraries in an efficient, user-friendly manner that does not interfere with their enjoyment of the content. Some users may also enjoy receiving suggestions to experience new media content with which they had not previously been familiar. These are generally the types of environment in which embodiments of the invention can be used.

For example, many people enjoy consuming media content, such as listening to audio content or watching video content, while running or engaging in other repetitive-motion activities. Examples of audio content include songs, albums, podcasts, audiobooks, etc. Examples of video content include movies, music videos, television episodes, etc. Using a mobile phone or other media-playback device a person can access large catalogs of media content. This nearly limitless access to media content introduces new challenges for users. For example, it may be difficult to find or select the right media content that complements a particular moment during a run or other repetitive-motion activity.

SUMMARY

In accordance with an embodiment, described herein is a system for multi-track playback of media content, including: a media device, including a processor; a user interface, provided at the media device, which displays a visual array of media options, wherein each media option is associated with one or more media content items, including one or more music, video or other media content, that can be streamed to or played on the media device; a playback logic, provided within the media device, which is configured so that, while a selected point or region is determined by the user interface as being moved in response to user input, within the visual array of media options, the system determines media options that are proximate to the selected point or region, and adjusts playback parameters for corresponding media content items, by crossfading or otherwise combining playback to reflect the media options relative distances from the selected point or region; and a tempo logic, provided within the media device, which is configured to provide or receive a selected tempo and provide the one or more media content items associated with the selected tempo.

DETAILED DESCRIPTION

As described above, today's consumers of digital media enjoy the ability to access a tremendous amount of media content, such as music and videos, at any location or time of day, using a wide variety of computing systems, handheld entertainment devices, smartphones, or other types of media device. However, with the increase in the amount of media content available, there exists the challenge of how to best provide access to that content.

To address this, in accordance with an embodiment, described herein is a system and method for multi-track playback of media content. A media device includes a user interface, which is adapted to display a visual array of media options, for example as a two-dimensional grid, or a list. The user interface can be touch-sensitive, or otherwise allow a user to select or explore a point or region within the visual array. Each media option is associated with one or more media content items that can be streamed to and/or played on the media device. While the user moves the selected point or region, for example by moving their finger over the media options, the system determines media options that are proximate to the selected point or region, and adjusts playback parameters for corresponding media content items, such as their relative playback volumes, by crossfading or otherwise combining playback to reflect the media options relative distances from the selected point or region.

In some examples described herein, the visual array of media options includes one or more media content items selected or otherwise associated with a user's current activities, such as repetitive-motion activities like swimming, biking, running, rowing, and other activities.

Figure 1:
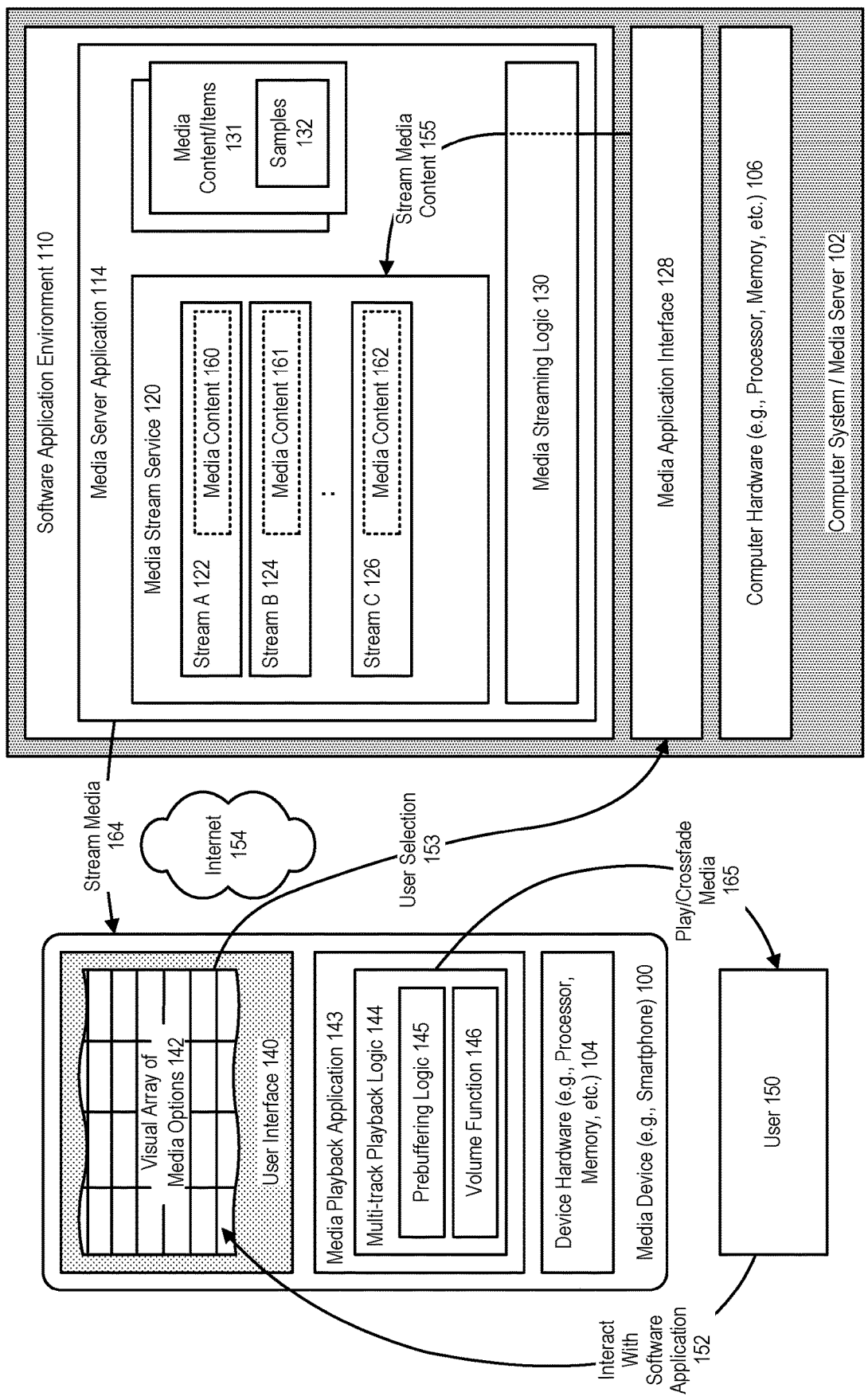
FIG. 1 illustrates a system for multi-track playback of media content, in accordance with an embodiment.

FIG. 1 illustrates a system for multi-track playback of media content, in accordance with an embodiment.

As shown in FIG. 1, in accordance with an embodiment, a media device or player 100, for example a computing system, handheld entertainment device, smartphone, or other type of media device capable of playing media content, can be used to play media content that is provided by a computer system operating as a media server 102, or from another system or peer device.

Each of the media device and the computer system operating as the media server can include, respectively, one or more physical computer or hardware resources 104, 106, such as one or more processors (CPU), physical memory, network components, or other types of hardware resources.

In accordance with an embodiment, the media server can include an operating system or other processing environment which supports execution of a software application environment 110, including a media server application 114 which can be used, for example, to stream music, video, or other forms of media content. A media stream service 120 can be used to buffer media content, for streaming to one or more streams 122, 124, 126. A media application interface 128 can receive requests from media devices or other systems, to retrieve media content from the media server.

Media content or items 131 (generally referred to herein as media content items), and/or samples 132 associated with the media content items, can be provided, for example, within a database or repository, or can be received at the media server from another source.

In accordance with an embodiment, the samples can be snippets that are determined by a media content producer (e.g., a record label) to best reflect a particular media content (e.g., a particular song track) created by that content producer. For example, a snippet may be a particularly recognizable portion of a particular song. Similarly, a video content snippet may be a particularly recognizable portion of a particular video. In accordance with various embodiments, other types of media samples or snippets, or previews can be used.

For example, in accordance with an embodiment, the system can use 30, 60, or 90 second audio-preview snippets for every song track. Longer snippets can provide a sufficient audio impression for the user of tuning into a particular track and being able to hear it till the end, after which the player can continue in playing back whatever is next in that context, providing an "on-demand" perception.

A media streaming logic 130 can be used to retrieve or otherwise access the media content items, and/or the samples associated with the media content items, in response to requests from media devices or other systems, and populate the media stream service with streams of corresponding media content data that can be returned to the requesting device.

As described above, in accordance with an embodiment, the media device can be a computing system, handheld entertainment device, smartphone, or other type of device that can playback media content. Although in FIG. 1 only a single media device and media server is shown, in accordance with an embodiment, the media server can support the simultaneous use of multiple media devices, and/or the media device can simultaneously access media content at multiple media servers.

In accordance with an embodiment, the media device can include a user interface 140, which is adapted to display or otherwise provide a visual array of media options 142, for example as a two-dimensional grid, a list, or other visual array format, and determine a user input. Examples of various visual arrays are described in further detail below.

Selecting a particular media option within the visual array can be used as a request or instruction to the media server application to stream or otherwise return a corresponding particular item of media content.

For example, in accordance with various embodiments, the software application environment at the media server can be used to stream or otherwise communicate music, video, or other forms of media content to the media device, wherein the user interface at the media device is adapted to display a plurality of music or video titles that correspond to music or videos stored as media content items in a database or repository at the media server.

In accordance with an embodiment, the media device can include a media playback application 143, together with a multi-track playback logic 144, prebuffering logic 145, and playback volume function 146, which can be used to control the playback and crossfading of media content items and/or samples that are received from the media server application, for playback by the media device, as described in further detail below.

In accordance with an embodiment, the prebuffering logic enables a portion of each media content item, sample, or snippet, to be pre-buffered at the media device, as decided by the multi-track playback logic. While media options are being prepared for display, their related media content can be pre-buffered at the same time, allowing for a playback experience that, from the user's perception, seems immediate.

In accordance with an embodiment, a user 150 can interact 152 with the application user interface and issue requests, for example the playing of a selected music or video item on their media device.

The user's selection of a particular media option can be communicated 153 to the media server application, via the media application interface. The media server application can then stream corresponding media content 155, including one or more streams of media content data 160, 161, 162, and subsequently stream 164 or otherwise communicate the, e.g., selected music, video, or other form of media content, to the user's media device. In accordance with an embodiment, pre-buffering requests from the media device can also be communicated to the media server application via the media application interface.

At the media device, in response to the user's interaction with the user interface, the media playback application, multi-track playback logic, and playback volume function can combine, crossfade, or otherwise play 165 the requested media content to the user, for example by playing back one or more music or videos on the media device, as described in further detail below.

Figure 2:
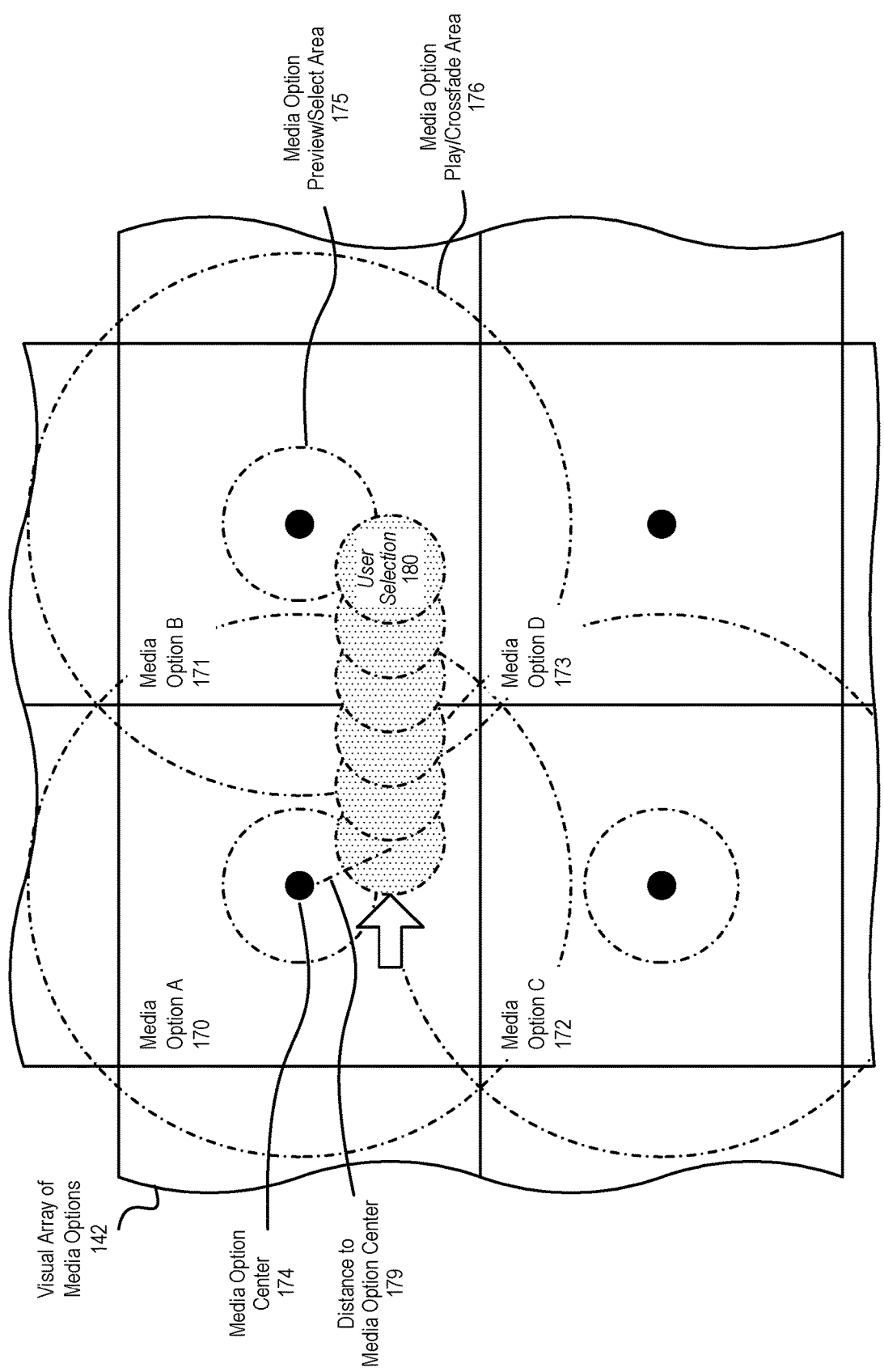
FIG. 2 illustrates multi-track playback of media content, in accordance with an embodiment.

FIG. 2 illustrates multi-track playback of media content, in accordance with an embodiment.

As shown in FIG. 2, in the example illustrated therein, four media options A (170), B (171), C (172), and D (173) are visualized as grid tiles, each of which has a media option center 174 (illustrated in the figure as a point), a relatively smaller media preview/select area 175 that is centered on the media option center, and a relatively larger media play/crossfade area 176 that generally covers the media option, and, depending on the particular implementation, can also extend to cover portions of other media options.

In accordance with an embodiment, a plurality of media options, for example a set of song tracks, a music playlist, or the contents of an album or a media library, can be represented on the user interface as a two-dimensional visual array, wherein the plurality of media options can be provided as an array of tiles, and wherein each tile can be associated with a particular visualization, for example a cover art identifying a represented song track.

In accordance with other embodiments, other forms of visualization can be used for the media options, for example texts, colors, images, or animations. While a selected point or region is moved within the grid of media options, the visualization or appearance of those media options that are proximate to the selected point or region can be modified, for example by varying their opacity, to reflect their status as proximate media options.

For example, in accordance with an embodiment, the opacity of a particular point or region, including the closest media option/tile and/or proximate media options/tiles, can be modified to render the closest or proximate media options to a selected point or region in a more visible manner than other (not selected, or not proximate) options/tiles.

In accordance with an embodiment, a user can provide input as a user selection of a point or region 180. In accordance with an embodiment, the user interface can be a touch-sensitive user interface, which recognizes input in the form of touch, for example the position of a user's finger or a stylus upon the user interface, to determine the selected point or region within the visual array of media options. Similarly, the user interface can determine the selected point or region as it is being moved, in response to a user input, within the visual array of media options. In the case of a mouse-based interface, the input can be provided by a mouse-down event.

In accordance with an embodiment, the system can, upon receiving the user input, initialize playback of those media options associated with the selected point or region. Selected media options (e.g., music or song tracks) can be played simultaneously according to a playback volume function, wherein playback parameters, such as the playback volume depends on the distance between the point of input and a specified point of the media option's (e.g., the song track's) array or tile visualization.

Figure 3:
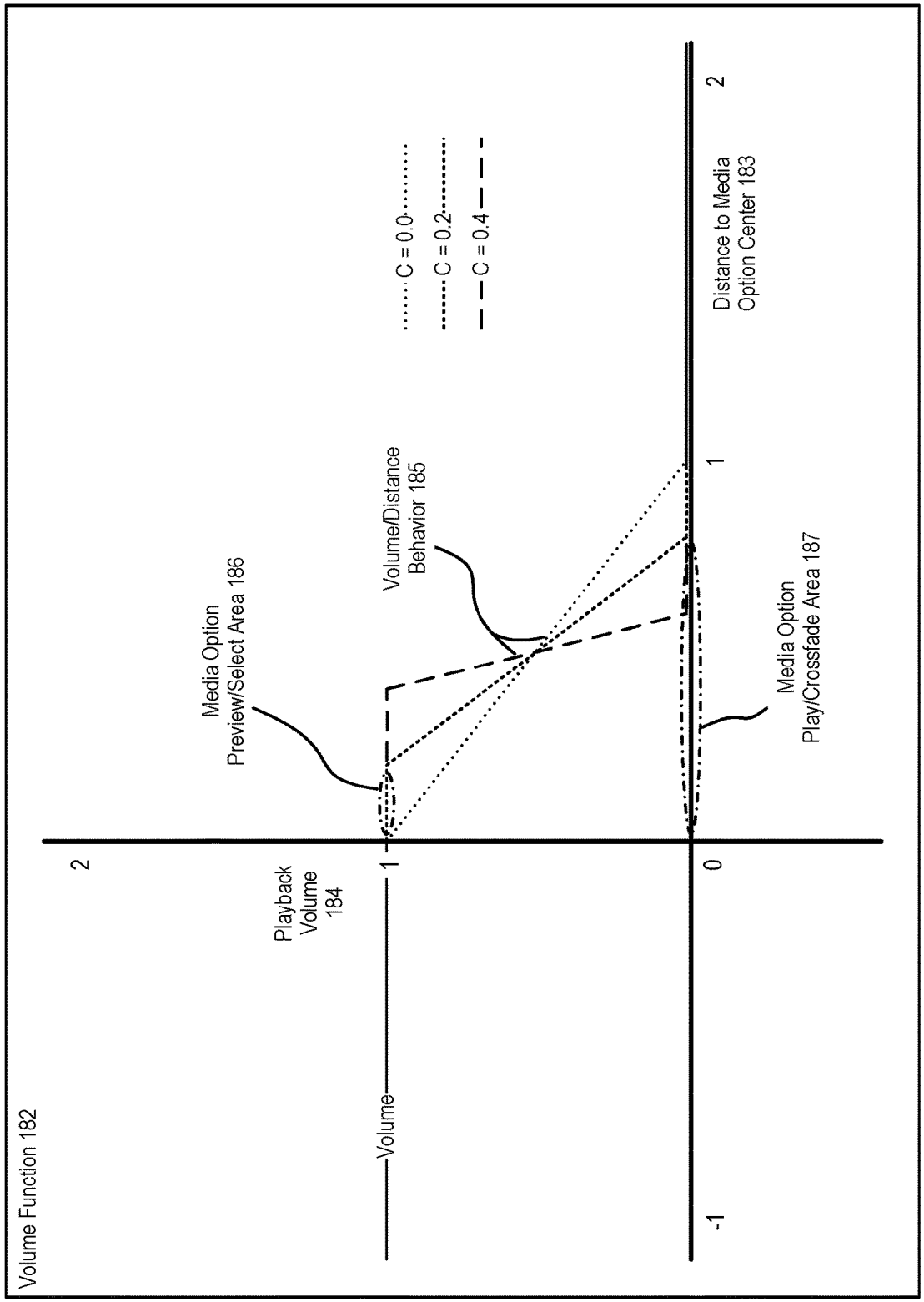
FIG. 3 illustrates an example of a playback volume function, in accordance with an embodiment.

FIG. 3 illustrates an example of a playback volume function 182, in accordance with an embodiment. In accordance with an embodiment, the playback volume of a media content item can be determined as a function of distance, for example:

$$y=\max(0,\min(1,((x-0.5)/2(C-0.5))+0.5))$$

wherein x represents the distance 183 between the selected point or region and a particular media option element, such as its center (for example when x=0, the user's finger is considered directly on the center of the particular media option, whereas when x=1, the user's finger is on a media option that is adjacent to the particular media option);

y represents a playback volume 184 (for example, 0 being silent, and 1 being a maximum or full playback volume); and C is a constant which reflects a distance from a particular media option's center that still results in full playback volume, such as the preview/select area described above.

As shown in FIG. 3, depending on the value used for C (examples of which for C=0.0, C=0.2, and C=0.4 are illustrated), different volume/distance behaviors 185 can be defined, which can be used to determine the size of the media preview/select area 175, the size of the media play/crossfade area 176, and the crossfading behavior, to address the needs of a particular implementation, or to suit a desired user experience.

The example illustrated in FIG. 3 is provided for purposes of illustration. In accordance with other embodiments, or to address the needs of other implementations, other types of playback volume functions, including the use of different functions, criteria, and constants, can be used.

In accordance with an embodiment, in the case of a visual array representation, such as a grid, that uses a plurality of tiles, the system can use the middle point of a tile as a point of calculating distance 179 from the selection point or region. In accordance with an embodiment, if the distance is zero, then the system considers that determination to be an actual selection by the user of that media option (e.g., that song track). In accordance with an embodiment, since it may be difficult for a user to precisely select the center of a tile, an area (e.g., 20-50%) of each tile, generally corresponding to the media preview/select area in FIG. 2, can be considered as centered on that particular option.

In accordance with an embodiment, if the selected point or region is more than one tile size away from a particular media option, then the playback volume of that particular media option is set to zero. In accordance with an embodiment, a two-dimensional grid can measure relative distance along both x and y axes. In the case of a one-dimensional array, for example a vertical list, then the system need only determine relative distance along one axis (e.g., the y axis), since it will not matter where the finger is along the x axis within a particular tile.

In accordance with an embodiment, media content items (e.g., song tracks), that are assigned a playback volume value of zero, are not being played. In accordance with an embodiment, while the triggering user input still lasts (for example, the user explores the available media options by keeping their finger touching the screen while moving, or the mouse button is held down), changing the input position (e.g., moving the finger, or moving the mouse cursor respectively), the system will recalculate the relative combination of the media content in the output, providing an audio crossfading effect that is controllable by the user.

In accordance with an embodiment, after ending the triggering input (e.g., the user releasing their finger, or releasing the mouse button respectively), then depending on the particular implementation, the media content item that is nearest the last movement input may either continue to play, or the playback can stop.

In accordance with an embodiment, while displaying the grid tiles the media device can pre-buffer a specified number of bytes from the audio snippets, for example 1 to 5 seconds.

This enables the system, upon receiving a user input, to playback the track immediately using the pre-buffered data, and continue fetching the rest of it. This allows for minimal latency of starting the playback, which results in a very compelling user experience.

Listing 1 provides an exemplary pseudocode of a method for determining multi-track playback of media content, in accordance with an embodiment. The pseudocode shown therein is provided for purposes of illustration. In accordance with other embodiments, other methods of determining multi-track playback of media content can be used.

---
Listing 1
---

```
Number clamp(Number x)
{
    return max(0, min(1, x))
}
# Calculate the volume for a given media element and a selection
# position. The coordinate system is assumed to be normalized so
# that the distance between different media elements is 1.
Number calculateMediaPlaybackVolume(
    Vector mediaPosition,
    Vector selectionPosition)
{
    Number distance = |mediaPosition - selectionPosition|
    Number cappedDistance = 0.2
    return clamp((distance - 0.5) / 2(cappedDistance - 0.5) + 0.5)
}
```

---

In accordance with an embodiment, the system can determine if the distance between the user selection of a particular point or region, is less distant from the center of a media option than a defined distance. If it is, then the playback volume for that media option is set to a relative value of 1 (within a range of 0 to 1), which makes it easier for the user to select a media option preview point without media noise from nearby media options. The linear distance of the user selection can be determined to be 1 when the user selection is within the preview/select area, and taper off to 0 at a distance generally corresponding to the play/crossfade area.

Having calculated a clamped distance of the user selection with respect to each of a plurality of media options, the system can then determine relative playback volume based on that distance, with shorter distances having higher playback volume, and longer distances having lower playback volume.

For example, as shown in Listing 1:

Number distance=|mediaPosition−selectionPosition|

In accordance with an embodiment, if the distance from a selection to the media element's position is less than a cappedDistance, the volume will be 1, which makes it easier to hit the preview point without hearing noise from tracks nearby. In order for this to work properly, the volume must be zero when distance is more than 1-cappedDistance; otherwise the media element could be playing when another element should be the only one being played back. In this example, the value for cappedDistance must be within (0, 0.5).

Listing 1 illustrates a clamped linear function that meets the following requirements:

$0 \le f(x) \le 1$ (i.e., the volume is never less than silent, or more than full volume);

$f(x)+f(1-x)=1$ (i.e., as the user continually moves the selection between the adjacent media elements, the sum of the volumes of those two media elements is full volume);

f is monotonically decreasing (i.e., as the user moves the selection away from a media element the volume never increases); and f(cappedDistance)=1 (i.e., the volume at this distance is at max even when the selection isn't exactly at the very center of the media element).

In accordance with an embodiment, as a visualization feature, while the user moves the selected point or region, for example by moving their finger over the media options, the opacity of the tiles can also be modified using a distance-based function similar to the one used to calculate playback volume.

Figure 4B:
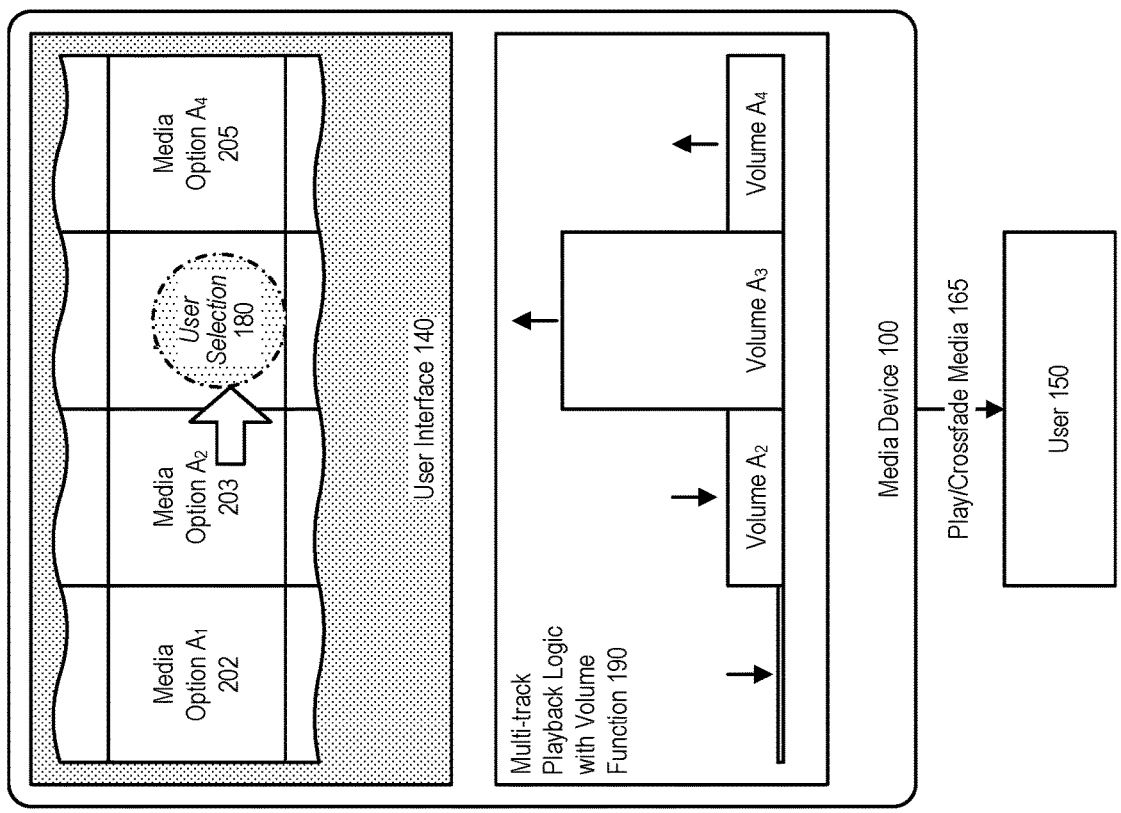
FIGS. 4A-4B further illustrates multi-track playback of media content, in accordance with an embodiment.
Figure 4A:
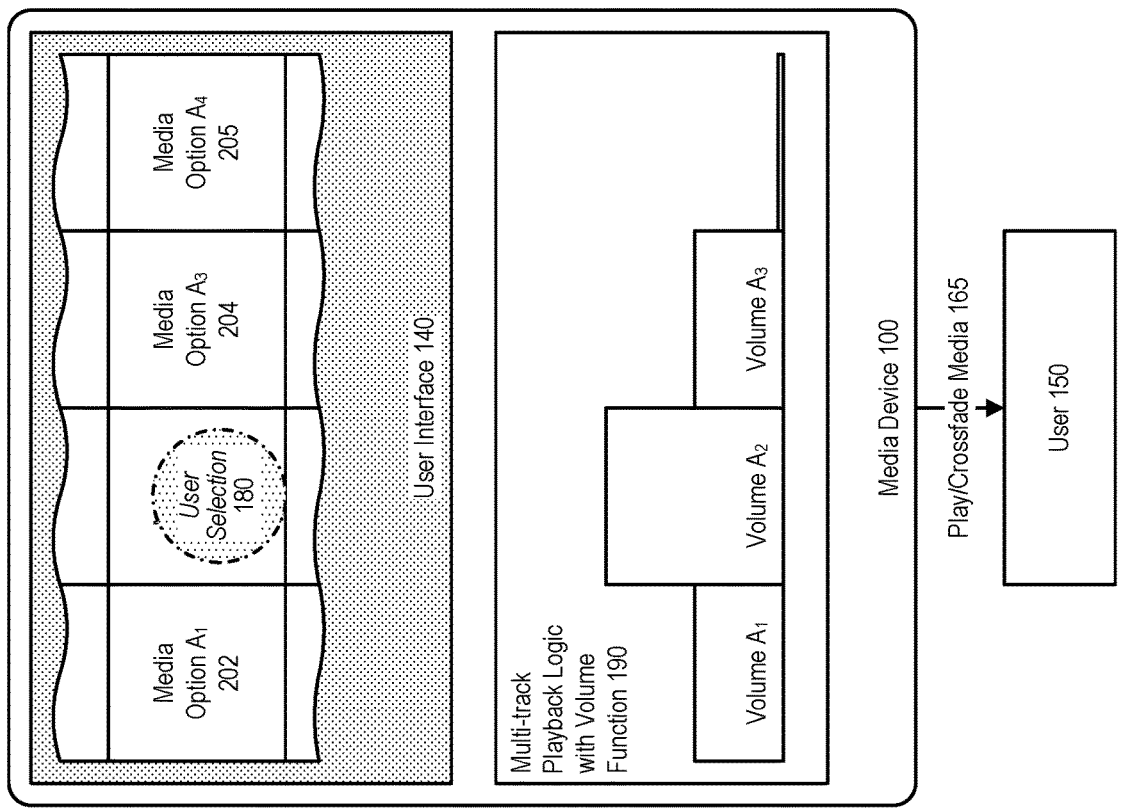

FIGS. 4A-4B further illustrate multi-track playback of media content, in accordance with an embodiment.

As shown in FIG. 4A, in the example user interface illustrated therein, a visual array of media options $A_1$ through $A_4$ (202-205) are shown, each of which media options is associated with one or more media content items.

A user can make a selection of a particular media option, for example by placing a mouse cursor or some other selector, at a point or region within the visual array. As described above, in accordance with an embodiment, the user interface can be a touch-sensitive user interface, which recognizes input in the form of touch, for example the position of a user's finger or a stylus upon the user interface, to determine the selected point or region within the visual array grid of media options.

In response to receiving an input from the user interface, the multi-track playback logic can determine a set of one or more of the plurality of media options that are proximate to the selected point or region (in this example, media options $A_1$, $A_2$ and $A_3$), and, together with its playback volume function, adjust playback parameters, such as the playback volume 190 of the set of media content items associated with those media options, by crossfading or otherwise combining the playback of the set of media content items to reflect their relative distances from the selected point or region.

An output can then be provided as a played-back or crossfaded media, e.g., a set of crossfaded songs, to the user. In the example illustrated in FIG. 4A, the user may perceive $A_2$ as being dominantly played, with some crossfading from sources $A_1$ and $A_3$.

In accordance with an embodiment, as shown in FIG. 4B, while the user moves their, e.g., finger, stylus, mouse cursor or other selector, to change their selection, the system can determine a new point or region or selection, and a plurality of media options that are proximate to the new point or region (in this example, media options $A_2$, $A_3$ and $A_4$).

In response to receiving the input from the user interface, the multi-track playback logic, together with its playback volume function, can again adjust playback parameters, such as the playback volume of the set of media content items associated with those media options, by crossfading or otherwise combining the playback of the set of media content items to reflect their relative distances from the newly selected point or region. The output can then be provided as different played-back or crossfaded media to the user, e.g., as a different set of crossfaded songs.

For example, while the selected point or region is moved from that shown in FIG. 4A to that shown in FIG. 4B, the relative playback volume of media content item $A_1$ and $A_2$ are decreased (in this example the playback volume of $A_1$ is reduced almost to zero), while the relative playback volume of media content item $A_3$ and $A_4$ are increased, reflecting their relative distances from the selected point or region. Particularly, the relative playback volume of $A_3$ is increased almost to the exclusion of other media content items, reflecting the much shorter distance between $A_3$ and the user's selected point or region. In the example illustrated in FIG. 4B, the user may perceive as $A_3$ being dominantly played, with little or no contribution or crossfading from any other sources.

In accordance with an embodiment if, as shown in FIG. 4B, the user's finger is still held down and a sample associated with the media content for $A_3$ ends, then playback of that media content can be repeated from the beginning of the sample.

Visual Array Grid

Figure 5:
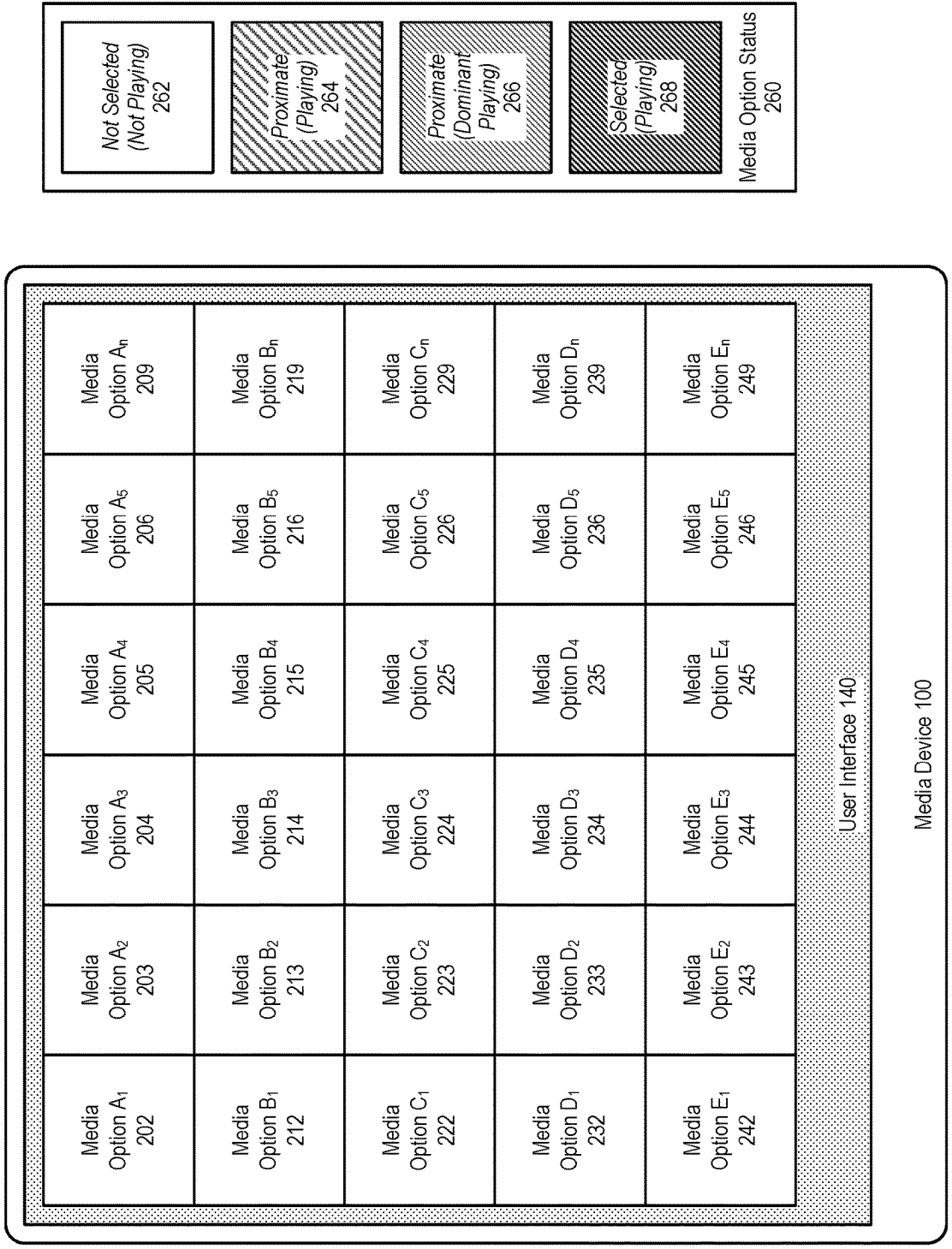
FIG. 5 illustrates a media device with an exemplary user interface which supports multi-track playback of media content, in accordance with an embodiment.

FIG. 5 illustrates a media device with an exemplary user interface which supports multi-track playback of media content, in accordance with an embodiment.

As shown in FIG. 5, in accordance with an embodiment, a user interface can display, for example, on a media device, a visual array of media options arranged as a two-dimensional grid, with rows and columns of media options visualized as tiles, here illustrated as $A_1$-$A_n$ through $E_1$-$E_n$ (202-249). Each of the media options is associated with one or more media content items that can be played on the device.

For purposes of illustration, each of the media options can be associated with a status 260 that reflects, from the user's perspective, whether that particular option's associated media content item is playing or not, and, if its associated media content item is playing then whether other media content items are being played at the same time.

For example, in accordance with an embodiment, media content items can be either not selected and not playing 262; proximate to a selected point or region and playing simultaneously with other media content items 264 (i.e., from the perspective of the user, with some perceptible crossfading of other media content items); proximate to a selected point or region but playing dominantly (i.e., from the perspective of the user, with little or no contribution or crossfading of other media content items) 266; or selected and playing (i.e., by itself with no other media content items playing simultaneously) 268.

Figure 6:
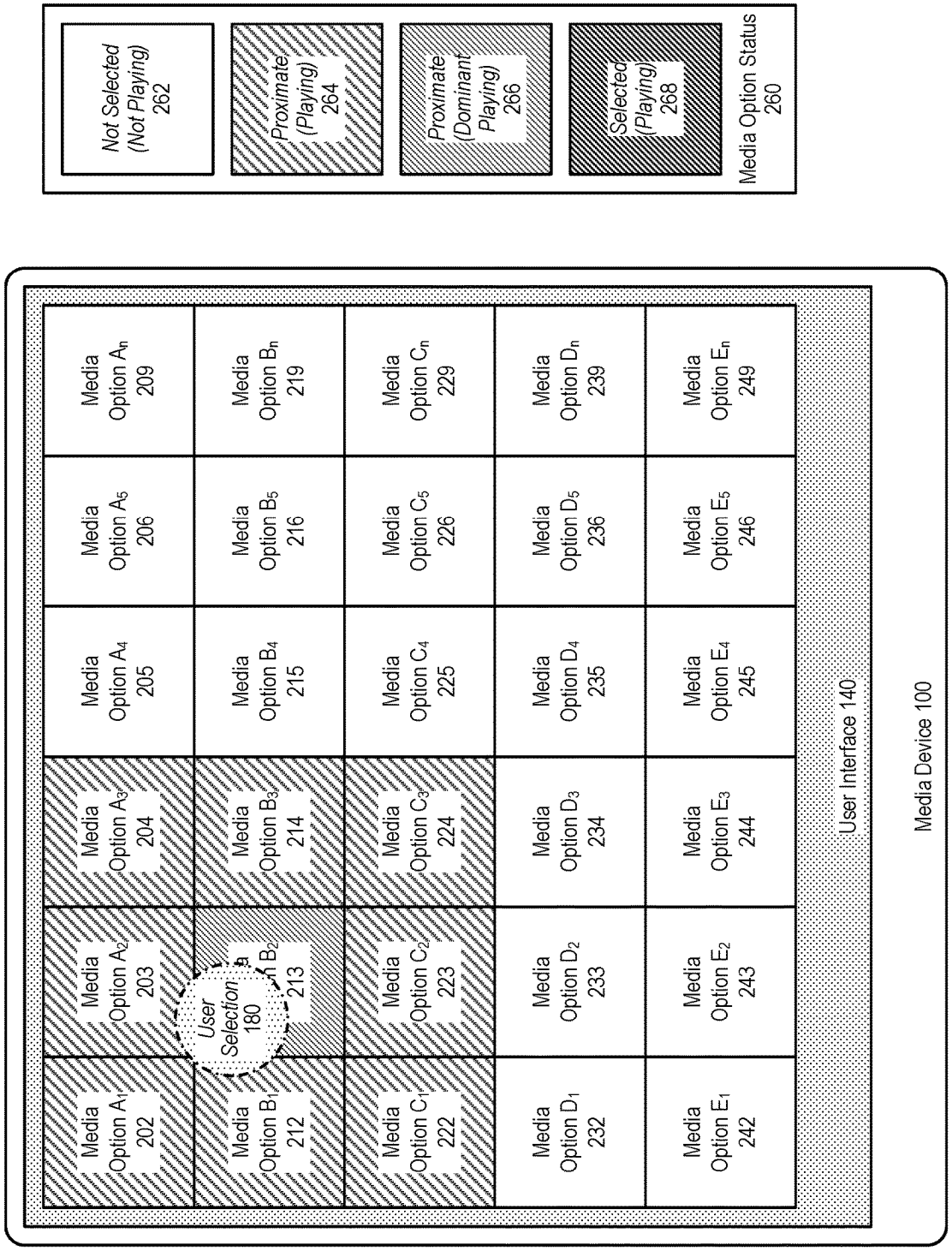
FIG. 6 further illustrates a user interface, in accordance with an embodiment.

FIG. 6 further illustrates a user interface, in accordance with an embodiment. As shown in FIG. 6, for example, a user may initially select a region (180) of the user interface generally located in the region of, but not precisely upon, media option $B_2$ (213), whose neighboring or proximate media options include $A_1$ (202), $A_2$ (203), $A_3$ (204), $B_1$ (212), $B_3$ (214), $C_1$ (222), $C_2$ (223) and $C_3$ (224).

In accordance with an embodiment, the multi-track playback logic can adjust the playback volume of media content items associated with each of these proximate media options, by crossfading or otherwise combining their playback, to reflect their relative distances from the selected point or region. The crossfaded or combined result can then be provided as a played-back media to the user.

In this example, the user may perceive an output from their media device in which media content $B_2$ is being dominantly played, with some perceptible combination of one or more of its neighboring or proximate media options as illustrated in FIG. 6.

Figure 7:
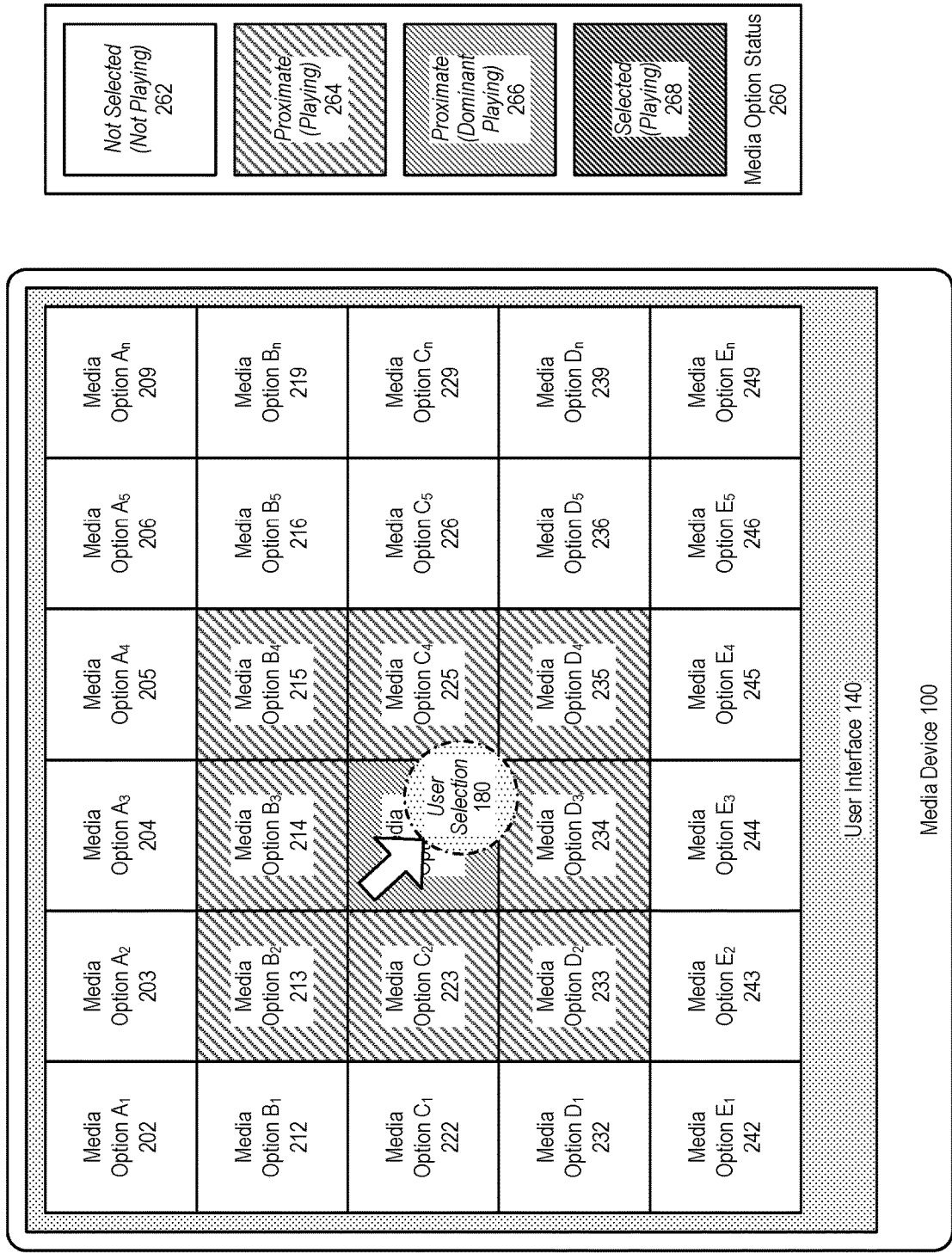
FIG. 7 further illustrates a user interface, in accordance with an embodiment.

FIG. 7 further illustrates a user interface, in accordance with an embodiment. As shown in FIG. 7, for example, a user may move their finger, mouse cursor, or other selector, to select or explore a new point or region of the user interface generally located in the region of media option $C_3$, but which is also proximate to media options $B_2$, $B_3$, $B_4$, $C_2$, $C_4$ (225), $D_2$ (233), $D_3$ (234) and $D_4$ (235). The multi-track playback logic can again adjust playback parameters, such as the playback volume of the set of media content items associated with these media options, by crossfading or otherwise combining their playback, to reflect their relative distances from the selected point or region.

In this example, the user may perceive an output from their media device in which media content $C_3$ is being dominantly played, with some perceptible combination of one or more of its neighboring or proximate media options as illustrated in FIG. 7.

Additionally, while the user moves their finger, mouse cursor, or other selector from the position shown in FIG. 6, to the position shown in FIG. 7, they may perceive a crossfading of media output as the multi-track playback logic gradually adjusts the playback volume of media content items from the initial output in which $B_2$ is being dominantly played, with some perceptible combination of one or more of its neighboring or proximate media options, to the subsequent output in which $C_3$ is being dominantly played, with some perceptible combination of one or more of its neighboring or proximate media options.

In accordance with an embodiment, a particular number of media options proximate to the selection point or region can be used, for example a window of nine (i.e., 3×3 tiles) proximate media options. However, in accordance with other embodiments, different numbers of media options proximate to the selection point or region can be used, and the chosen media options need not necessarily be in a square or other uniform pattern.

Figure 8:
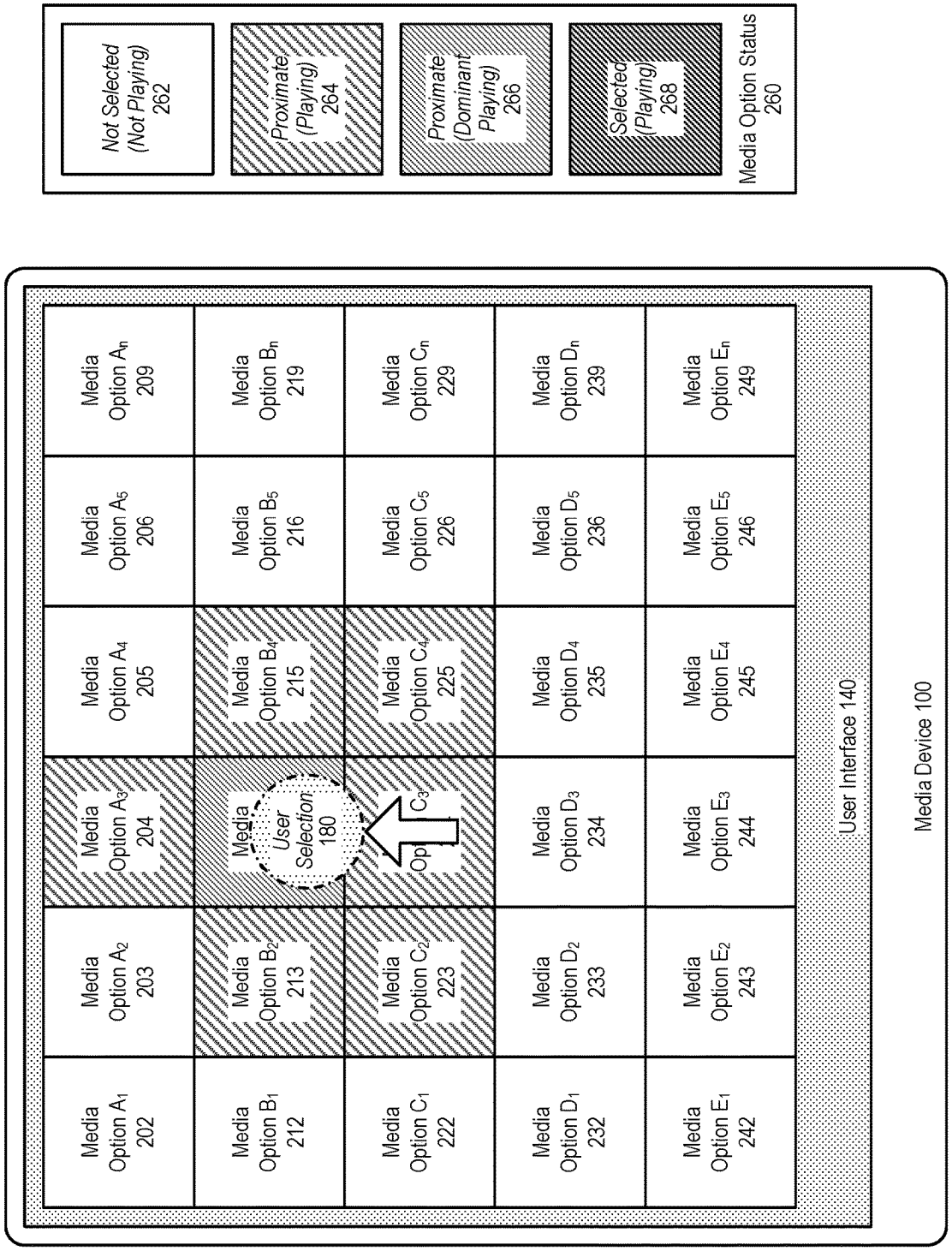
FIG. 8 further illustrates a user interface, in accordance with an embodiment.

FIG. 8 further illustrates a user interface, in accordance with an embodiment.

As shown in FIG. 8, for example, a user may again move their finger, mouse cursor, or other selector, to select or explore another new point or region of the user interface generally located at media option $B_3$, but which is also proximate to media options $A_3$ (204), $B_2$, $B_4$ (215), $C_2$, $C_3$ and $C_4$.

Again, the multi-track playback logic can adjust playback parameters, such as the playback volume of the set of media content items associated with these media options, by crossfading or otherwise combining their playback, to reflect their relative distances from the selected point or region, in this example using just seven media options.

Again also, the user may perceive a crossfading of media output as the multi-track playback logic gradually adjusts the playback volume of media content items from the original output in which $C_3$ is being dominantly played, to the subsequent output in which $B_3$ is being dominantly played.

Figure 9:
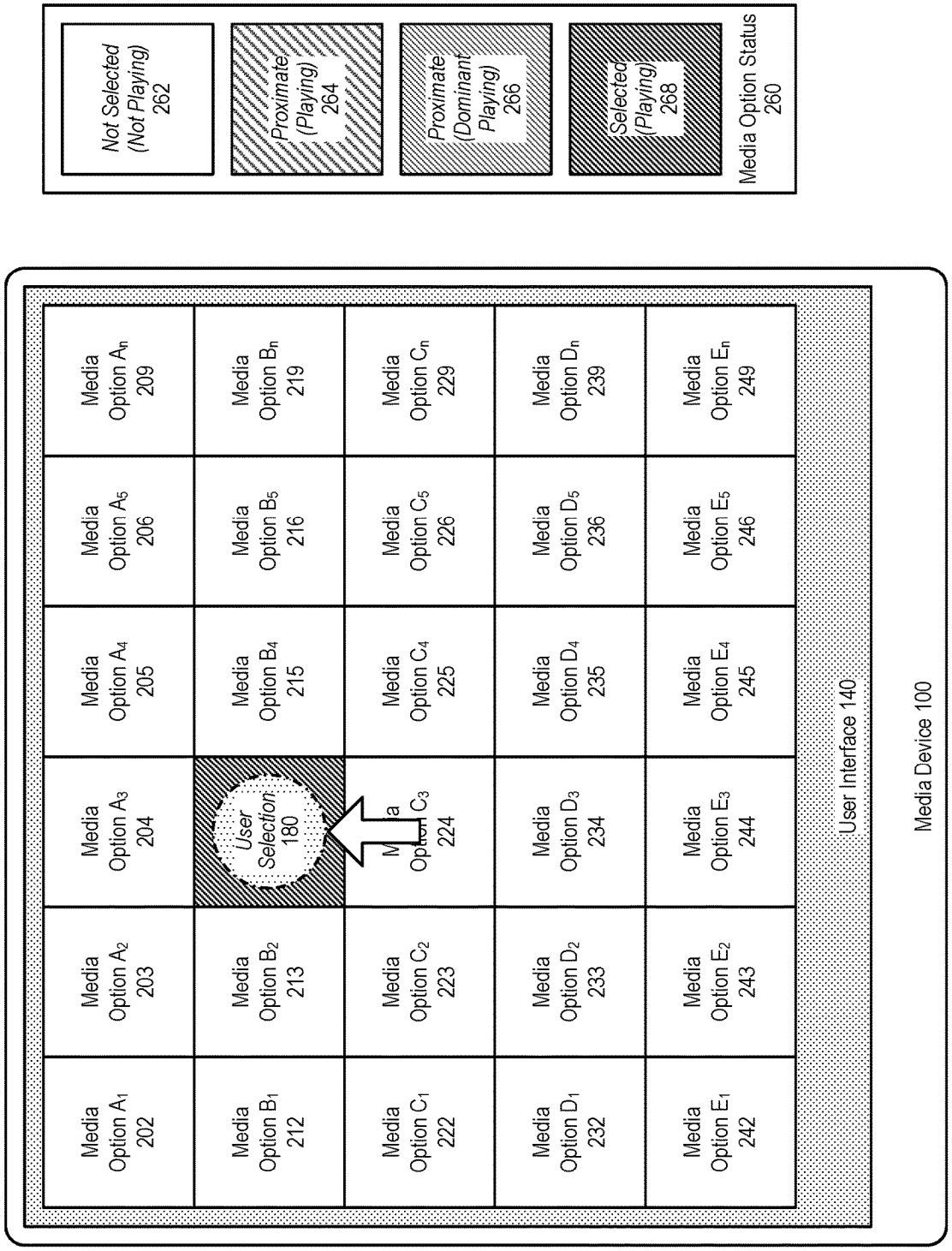
FIG. 9 further illustrates a user interface, in accordance with an embodiment.

FIG. 9 further illustrates a user interface, in accordance with an embodiment. As shown in FIG. 9, in accordance with an embodiment, if the user moves their finger, mouse cursor, or other selector, to select the center of a point or region of the user interface generally located at a media option, and leaves it there for a period of time, then in accordance with an embodiment, that media content item can be selected, and played by itself (i.e., from the perspective of the user, with no other media content items playing simultaneously).

Figure 10:
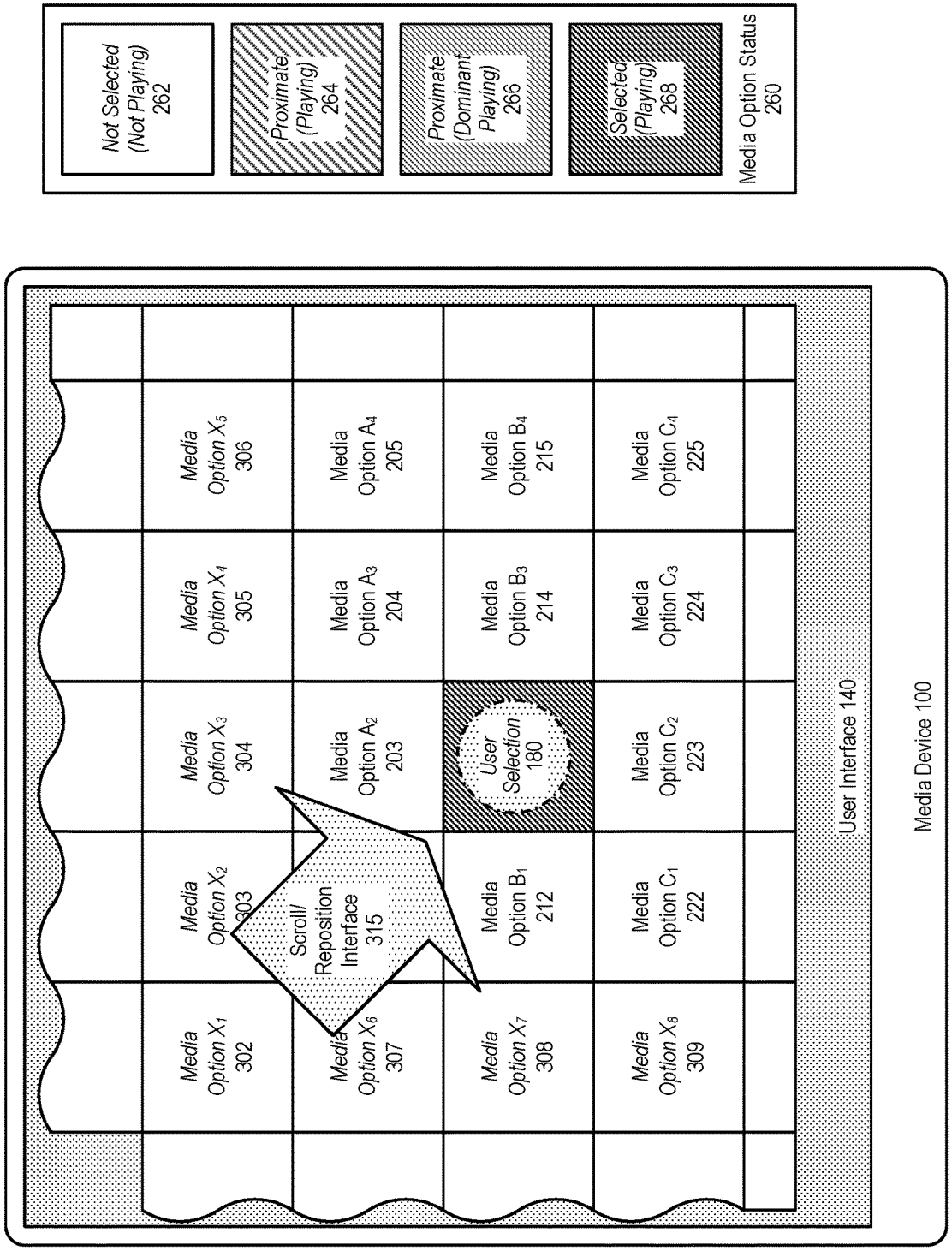
FIG. 10 further illustrates a user interface, in accordance with an embodiment.

FIG. 10 further illustrates a user interface, in accordance with an embodiment. As shown in FIG. 10, in accordance with an embodiment, while a media content item is selected and being played, the grid can be automatically scrolled or repositioned 315, both generally centering the currently selected point or region, and in this example displaying on the user interface new or additional media options $X_1$-$X_8$ (302-309), which can be subsequently selected by the user.

Figure 11:
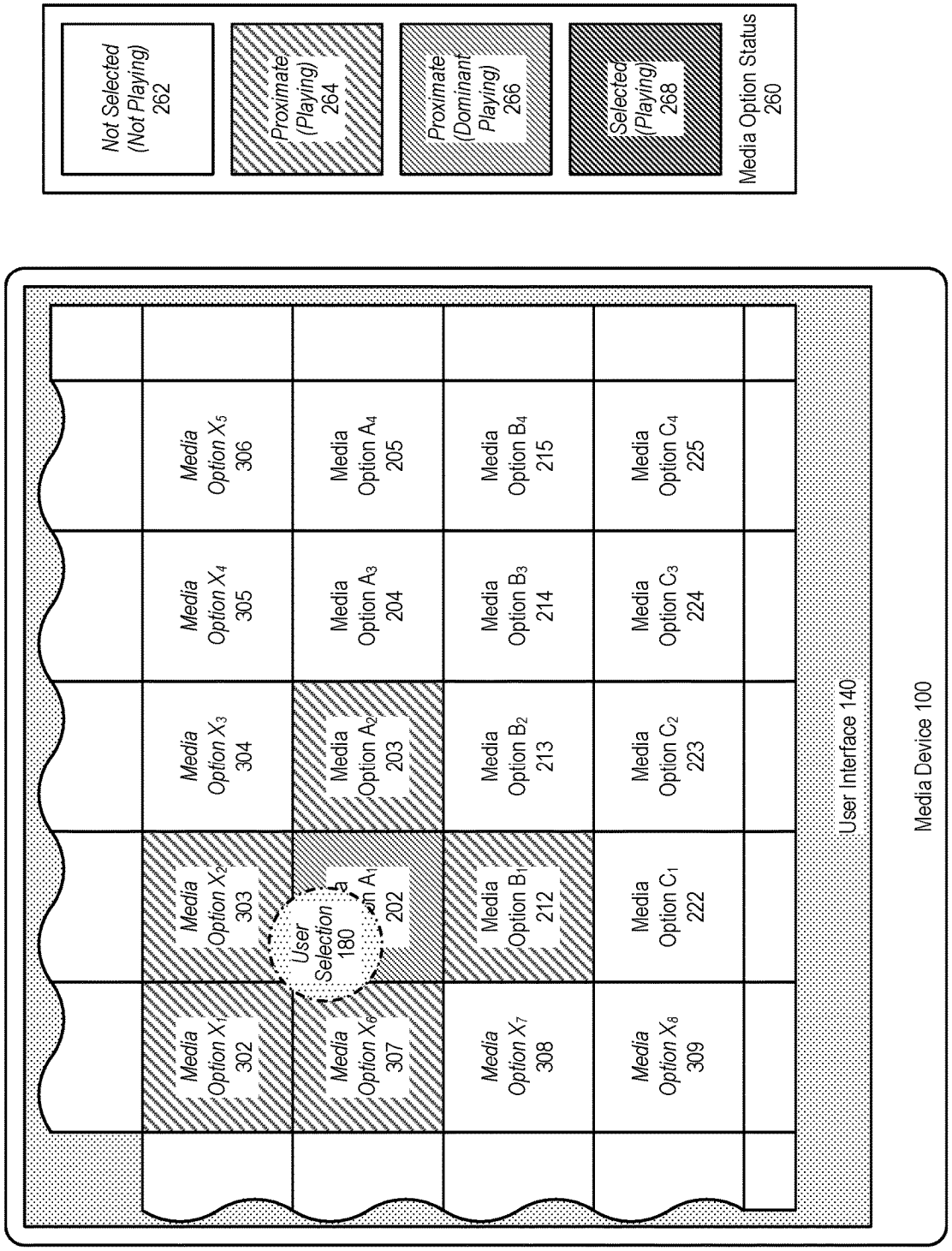
FIG. 11 further illustrates a user interface, in accordance with an embodiment.

FIG. 11 further illustrates a user interface, in accordance with an embodiment. As shown in FIG. 11, for example, a user may select a region of the user interface generally located at media options $A_1$ (202), with neighboring or proximate media options $A_2$, $B_1$, $X_1$ (302), $X_2$ (303) and $X_6$ (307).

The process can generally continue as described above, with the user continuing to move the selected point or region within the visual array, to further explore media options, and the playback of proximate media content items continually adjusted, by crossfading or otherwise combining their playback. For example, when the grid is automatically scrolled or repositioned, the new or additional media options can be explored by the user, or offered as suggestions to browse and experience new media content with which they had not previously been familiar.

In accordance with an embodiment, if the user's finger is lifted from the user interface, the device can, for example, play a song to its end, by appending media content to a previously-played sample or snippet, so that playback seamlessly flows from the end of the sample or snippet into the remainder of the song. If the sample is relatively long (e.g., 90 seconds) and located near the end of the song, the device can play the sample to its end. At the end, a next song can be chosen according to shuffle rules, a playlist, or other means.

In accordance with another embodiment, if the user's finger is lifted from the user interface, the sample or snippet can stop playing, and an original, e.g. song, return to being played. If the user immediately taps the same location, the device can play the last-selected media content from its beginning.

The examples provided above of various user interaction techniques are provided for purposes of illustration. In accordance with other embodiments, or to address the needs of other implementations, other types of user interaction techniques can be supported.

Alternative Visual Array Examples

Figure 12:
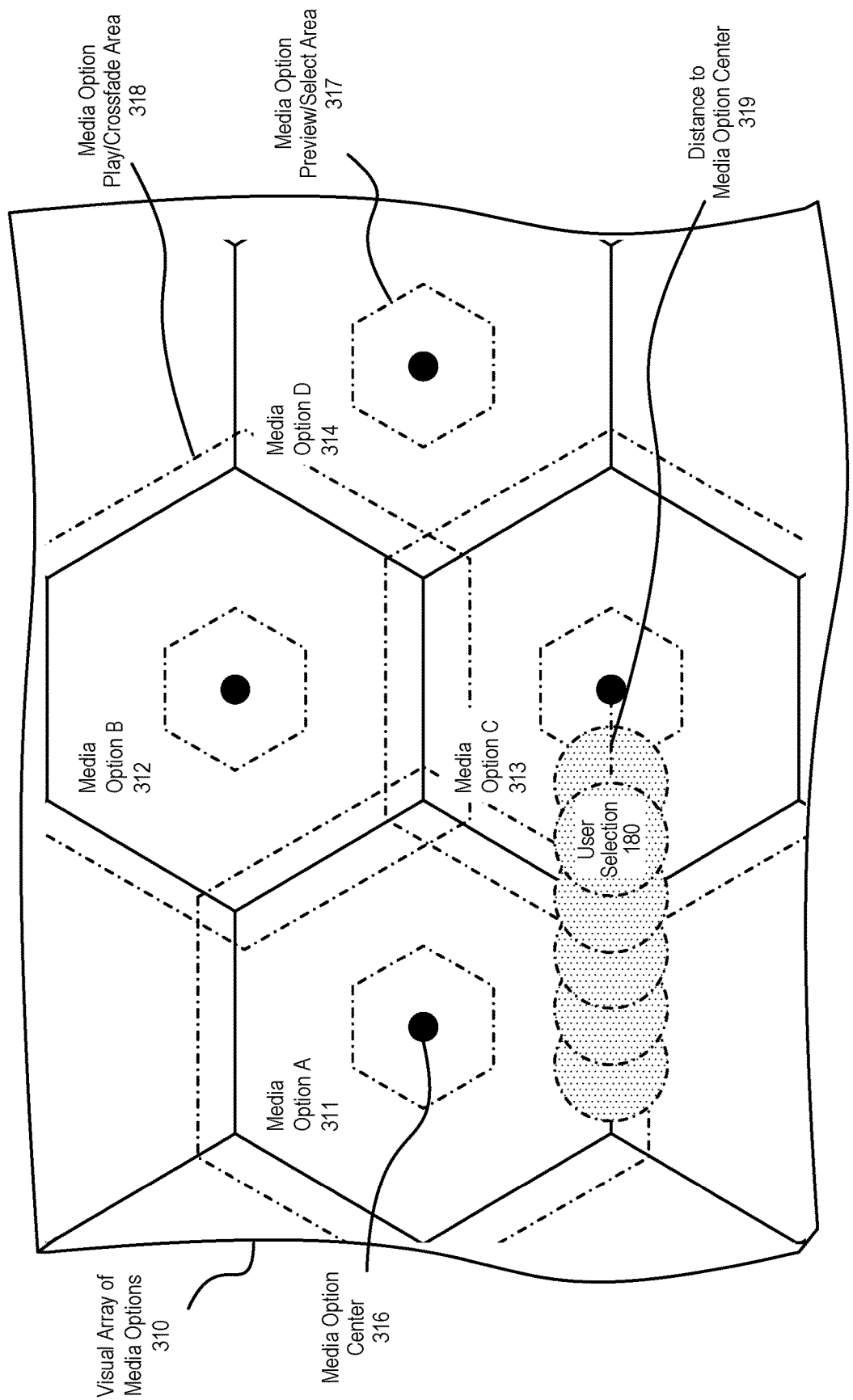
FIG. 12 illustrates an exemplary user interface, in accordance with an alternate embodiment.

FIG. 12 illustrates an exemplary user interface, in accordance with an alternate embodiment.

As shown in FIG. 12, in accordance with an embodiment, a user interface can display a visual array 310 of media options arranged as a two-dimensional grid of, in this example, hexagonal tiles, with media options A-D (311-314). As described above, each of the media options can have a media option center 316, a relatively smaller media preview/select area 317 centered on the media option center, and a relatively larger media play/crossfade area 318 that generally covers the media option, and, depending on the particular implementation, can extend to cover portions of other media options.

The system can use the middle point of a tile as a point of calculating distance 319 from the selection point or region, and adjusting the playback parameters, such as the playback volume for each media option, as described above.

The above are provided by way of example. In accordance with other embodiments, other types of user interface, visual array, and tile shapes can be used.

Scrollable List Visual Array

Figure 13:
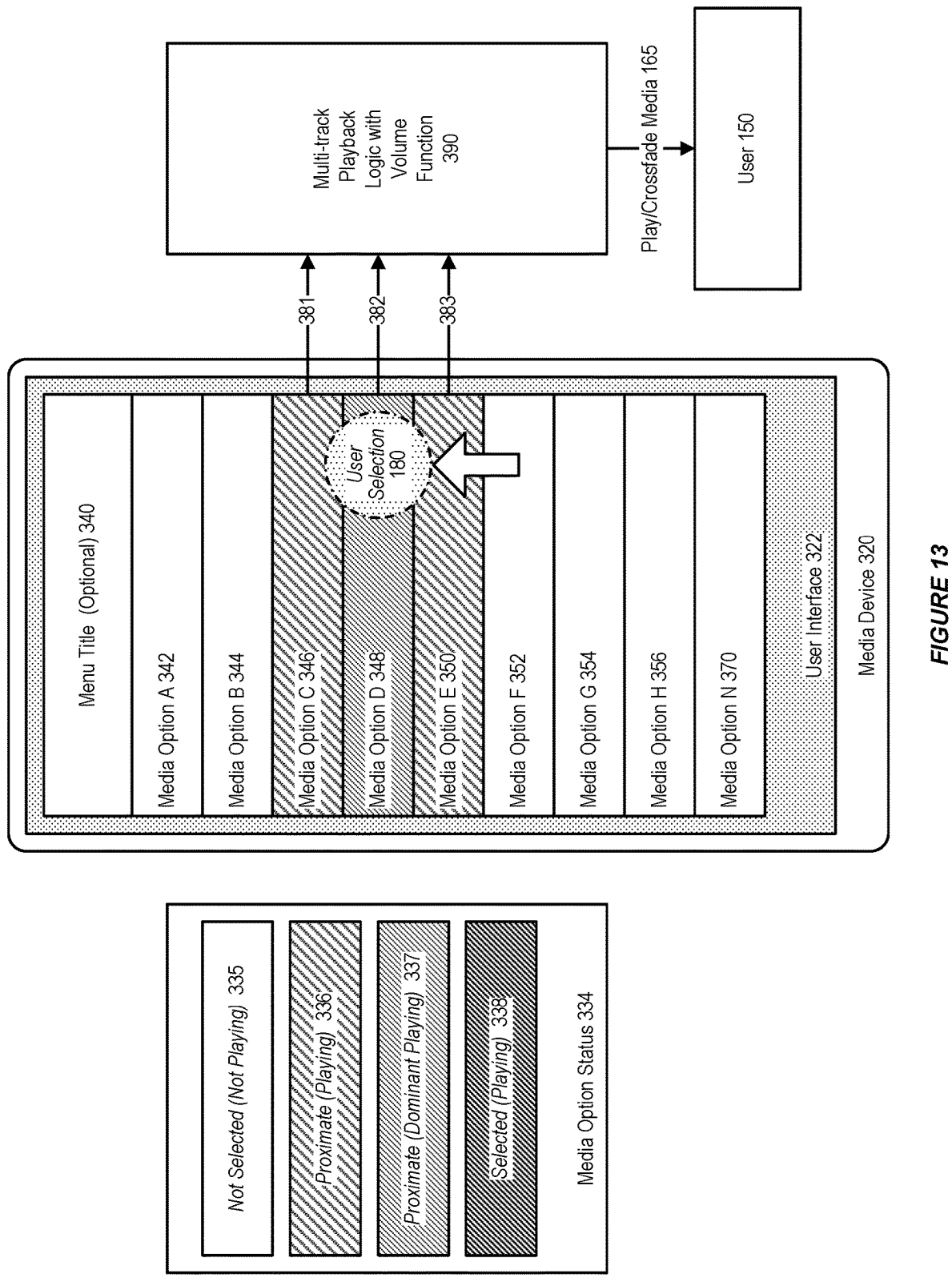
FIG. 13 illustrates a media device with an exemplary user interface which supports multi-track playback of media content, in accordance with an alternative embodiment.

FIG. 13 illustrates a media device with an exemplary user interface which supports multi-track playback of media content, in accordance with an alternative embodiment. As shown in FIG. 13, in accordance with an embodiment, a media device 320 having a user interface 322 can display an optional menu or other information 340, and a visual array of media options arranged in this example as a scrollable list A-N (342-370), each of which media options is associated with one or more media content items that can be played.

For purposes of illustration, each of the media options can be similarly associated with a status 334 that reflects, from the user's perspective, whether that particular option's associated media content item is playing, or not playing, and, if its associated media content item is playing then whether other media content items are being played at the same time; for example not selected and not playing 335; proximate to a selected point or region and playing simultaneously with other media content items 336; proximate to a selected point or region but playing dominantly 337; or selected and playing by itself 338.

In accordance with an embodiment, when none of the displayed media options (e.g., 342-370) are currently playing, an alternative media content can be played, which can then be paused, or its volume reduced completely, when any of the displayed options are transition to a playing status.

For example, a user can select a region proximate to media options C (346), D (348), and E (350), which causes those media contents to be retrieved, e.g., from the media server, and provided 381, 382, 383 to the multi-track playback logic with playback volume function 390, where the media contents can be played and crossfaded as described above, and provided to the user.

In accordance with an embodiment, when a menu of media options is displayed, the device can start to pre-buffer samples of, e.g. the songs represented by the media options in that menu. When a media option transitions from a "not playing" status to a "playing" status, playback can begin with the pre-buffered data, while the device streams more data and seamlessly move playback over to the streamed data. Streamed data can then be similarly buffered locally for a period of time, or until the user stops using the application.

Figure 14:
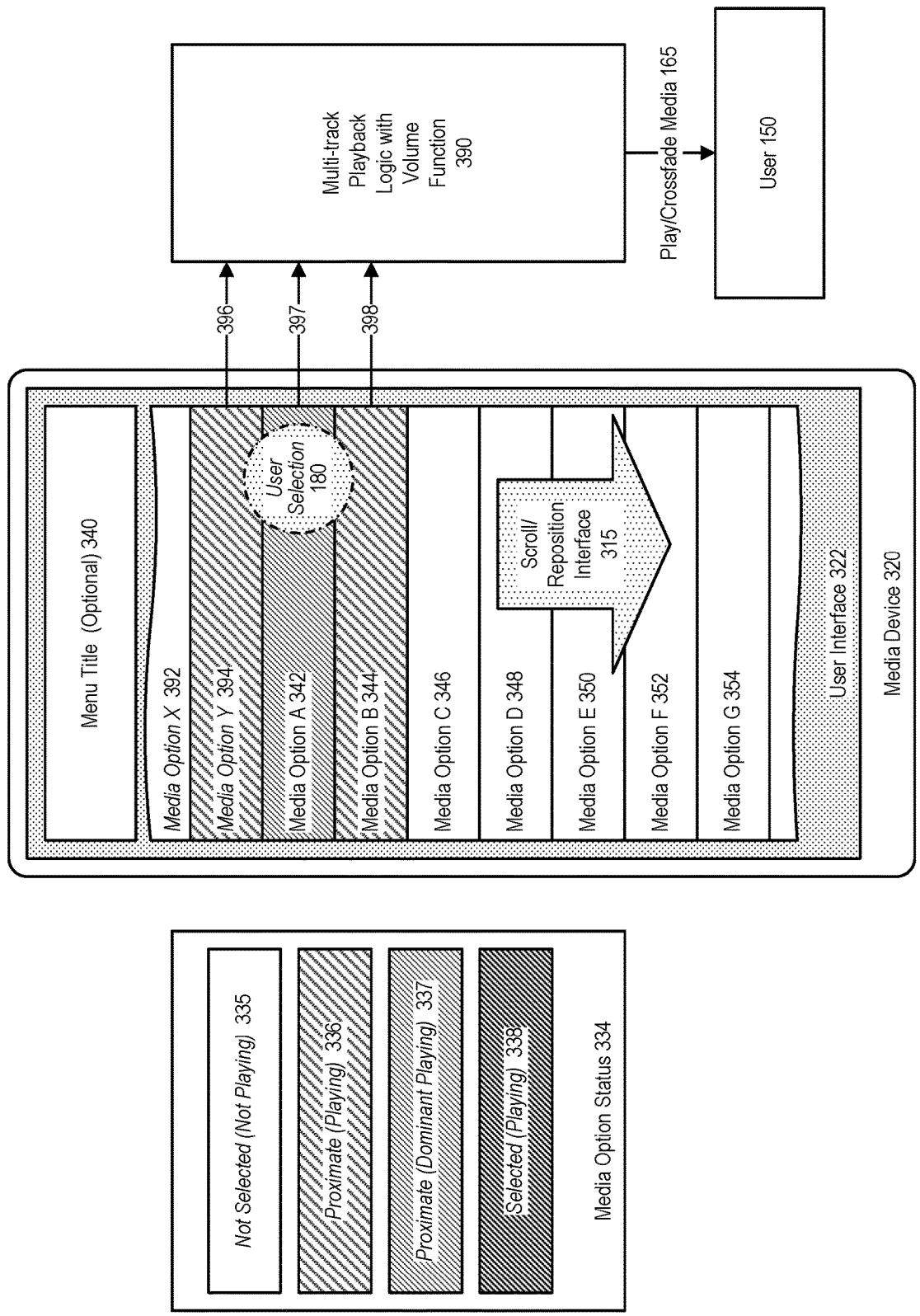
FIG. 14 further illustrates a media device, in accordance with an alternate embodiment.

FIG. 14 further illustrates a media device, in accordance with an alternate embodiment. As shown in FIG. 14, while a media content item is selected and being played, the list can be automatically scrolled or repositioned, for example centering the selected media option, and displaying on the user interface additional media options, such as X (392) and Y (394). A user may select or explore regions proximate to media options A (342), B (344), and Y, which causes those media contents to be retrieved from the media server and provided 396, 397, 398 to the multi-track playback logic with playback volume function where it can be played and crossfaded as described above, and provided to the user.

In accordance with an embodiment, the action of exploring a particular media option (e.g., A 342) causes the display to scroll down, without the user's finger having to move, and automatically allowing the user to explore, in this example, media option Y 394, while the list moves.

The process can generally continue as described above, with the user continuing to move the selected point or region within the visual array, to further explore media options, and the playback of proximate media content items continually adjusted, by crossfading or otherwise combining their playback.

Multi-Track Playback Method

Figure 15:
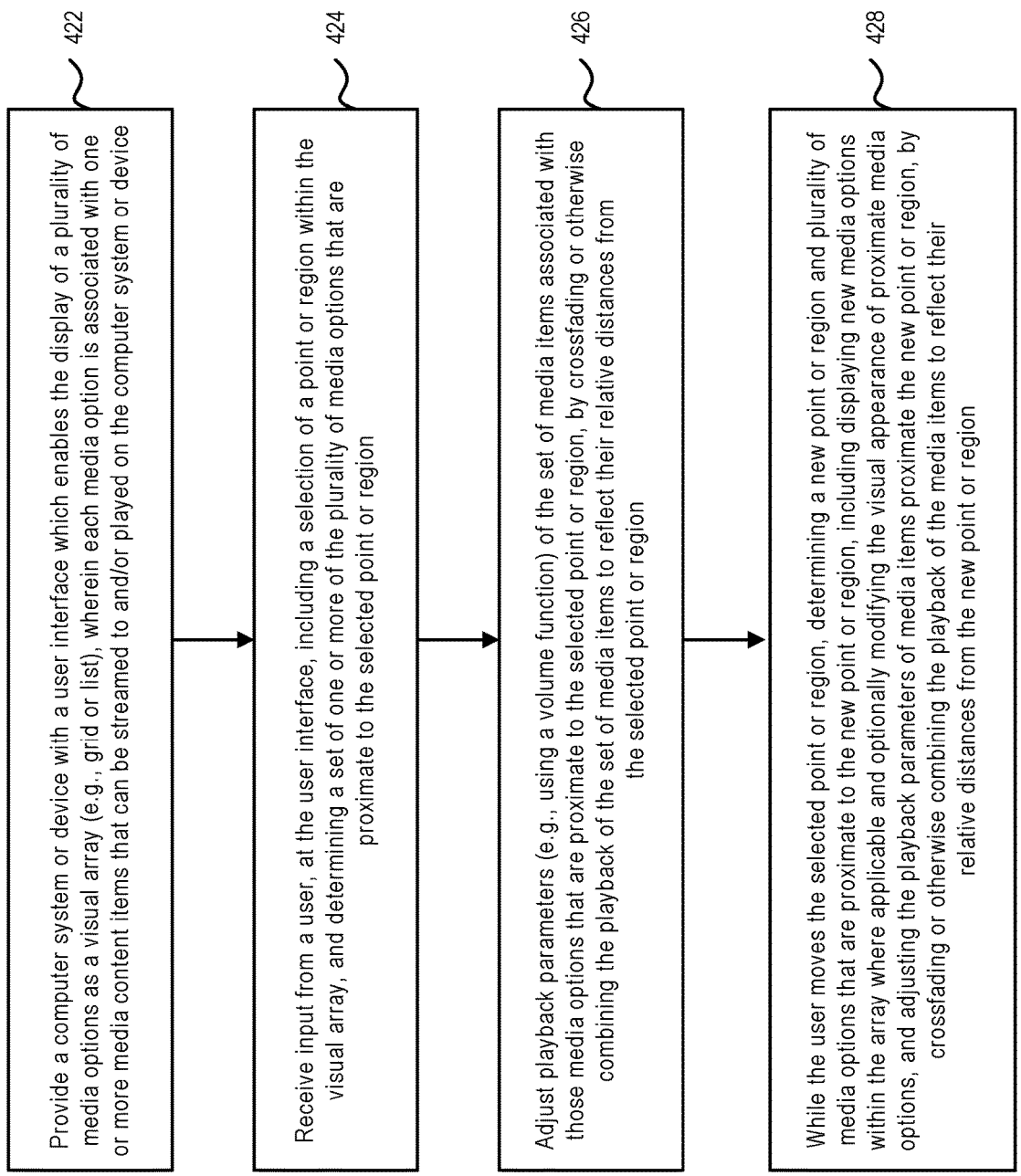
FIG. 15 is a flowchart of a method for multi-track playback of media content, in accordance with an embodiment.

FIG. 15 is a flowchart of a method for multi-track playback of media content, in accordance with an embodiment.

As shown in FIG. 15, at step 422, a computer system or device is provided with a user interface which enables the display of a plurality of media options as a visual array (e.g., a grid or list), wherein each media option is associated with one or more media content items that can be streamed to and/or played on the computer system or device.

At step 424, an input is received from a user, at the user interface, including a selection of a point or region within the visual array, which can be used to determine a set of one or more of the plurality of media options that are proximate to the selected point or region.

At step 426, the playback parameters (e.g., the playback volume) of the set of media content items associated with those media options that are proximate to the selected point or region, are adjusted by crossfading or otherwise combining the playback of the set of media content items to reflect their relative distances from the selected point or region.

At step 428, while the user moves the selected point or region, a new point or region and plurality of media options that are proximate to the new point or region is determined, including displaying new or additional media options within the visual array where applicable and optionally modifying the visual appearance of proximate media options. The playback of media content items proximate the new point or region are again adjusted, by crossfading or otherwise combining their playback to reflect their relative distances from the new point or region.

The process can continue with the user continuing to move the selected point or region and the playback of proximate media content items continually adjusted, by crossfading or otherwise combining their playback.

Figure 16:
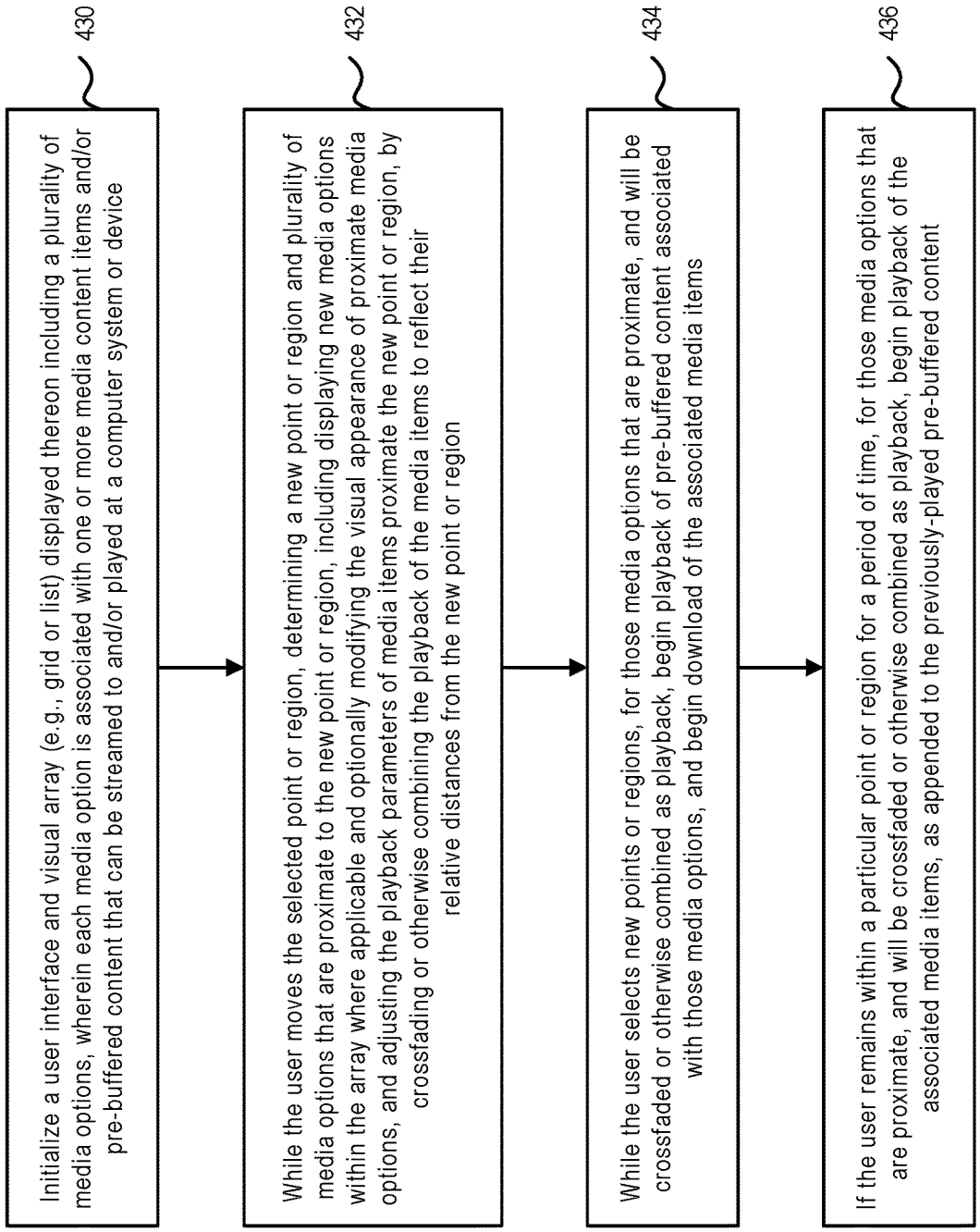
FIG. 16 is another flowchart of a method for multi-track playback of media content, in accordance with an embodiment.

FIG. 16 is another flowchart of a method for multi-track playback of media content, in accordance with an embodiment.

As shown in FIG. 16, at step 430, a user interface is initialized with a visual array displayed thereon including a plurality of media options, wherein each media option is associated with one or more media content items and/or pre-buffered content that can be streamed to and/or played on the computer system or device.

At step 432, while the user moves the selected point or region, a new point or region and plurality of media options that are proximate to the new point or region is determined, and the playback parameters of proximate media adjusted by crossfading or otherwise combining their playback to reflect their relative distances from the new point or region, as described above.

At step 434, while the user selects new points or regions, for those media options that are proximate to the new point or region, and will be crossfaded or otherwise combined as playback, the system can begin playback of pre-buffered content associated with those media options, and also begin download of the associated media content items.

At step 436, if the user remains within a particular point or region for a period of time, for those media options that are proximate, and will be crossfaded or otherwise combined as playback, the system begins playback of the associated media content items, as appended to the previously-played pre-buffered content.

Repetitive Motion Activities

Users of media-playback devices often consume media content while engaging in various activities, including repetitive motion activities. As noted above, examples of repetitive-motion activities may include swimming, biking, running, rowing, and other activities. Consuming media content may include one or more of listening to audio content, watching video content, or consuming other types of media content. For ease of explanation, the embodiments described in this application are presented using specific examples. For example, audio content (and in particular music) is described as an example of one form of media consumption. As another example, running is described as one example of a repetitive-motion activity. However, it should be understood that the same concepts are equally applicable to other forms of media consumption and to other forms of repetitive-motion activities, and at least some embodiments include other forms of media consumption and/or other forms of repetitive-motion activities.

The users may desire that the media content fits well with the particular repetitive activity. For example, a user who is running may desire to listen to music with a beat that corresponds to the user's cadence. Beneficially, by matching the beat of the music to the cadence, the user's performance or enjoyment of the repetitive-motion activity may be enhanced. This desire cannot be met with traditional media-playback devices and media-delivery systems.

In such examples, the user can use the media-playback device 100 to provide media content as the user performs the repetitive motion activity, such as running. The media-playback device 100 can be programmed to play media content for the user based on the user's cadence. In the example shown, the media content includes music with a tempo that corresponds to the user's cadence. The tempo (or rhythm) of music refers to the frequency of the beat and is typically measured in beats per minute (BPM). The beat is the basic unit of rhythm in a musical composition (as determined by the time signature of the music). Accordingly, in the example shown, the user's steps occur at the same frequency as the beat of the music.

For example, if the user is running at a cadence of 180 steps per minute, the media-playback device 100 may play a media content item having a tempo equal to or approximately equal to 180 BPM. In other embodiments, the media-playback device 100 plays a media content item having a tempo equal or approximately equal to the result of dividing the cadence by an integer such as a tempo that is equal to or approximately equal to one-half (e.g., 90 BPM when the user is running at a cadence of 180 steps per minute), one-fourth, or one-eighth of the cadence. Alternatively, the media-playback device 100 plays a media content item having a tempo that is equal or approximately equal to an integer multiple (e.g., 2×, 4×, etc.) of the cadence. Further, in some embodiments, the media-playback device 100 operates to play multiple media content items including one or more media content items having a tempo equal to or approximately equal to the cadence and one or more media content items have a tempo equal or approximately equal to the result of multiplying or dividing the cadence by an integer. Various other combinations are possible as well.

In some embodiments, the media-playback device 100 operates to play music having a tempo that is within a predetermined range of a target tempo. In at least some embodiments, the predetermined range is plus or minus 2.5 BPM. For example, if the user is running at a cadence of 180 steps per minute, the media-playback device 100 operates to play music having a tempo of 177.5-182.5 BPM. Alternatively, in other embodiments, the predetermined range is itself in a range from 1 BPM to 10 BPM.

Further, in some embodiments, the media-playback device 100 operates to play music having a tempo equal to or approximately equal to a user's cadence after it is rounded. For example, the cadence may be rounded to the nearest multiple of 2.5, 5, or 10 and then the media-playback device 100 plays music having a tempo equal to or approximately equal to the rounded cadence. In yet other embodiments, the media-playback device 100 uses the cadence to select a predetermined tempo range of music for playback. For example, if the user's cadence is 181 steps per minute, the media-playback device 100 may operate to play music from a predetermined tempo range of 180-184.9 BPM; while if the user's cadence is 178 steps per minute, the media-playback device 100 may operate to play music from a predetermined tempo range of 175-179.9 BPM.

Additional details on how the media-playback device 100 can be configured to automatically estimate a user's cadence and to select one or more media content with a given tempo is provided in U.S. Patent Application Ser. No. 62/163,840, titled CADENCE DETERMINATION AND MEDIA CONTENT SELECTION, filed on May 19, 2015, which is hereby incorporated by reference in its entirety.

Figure 17:
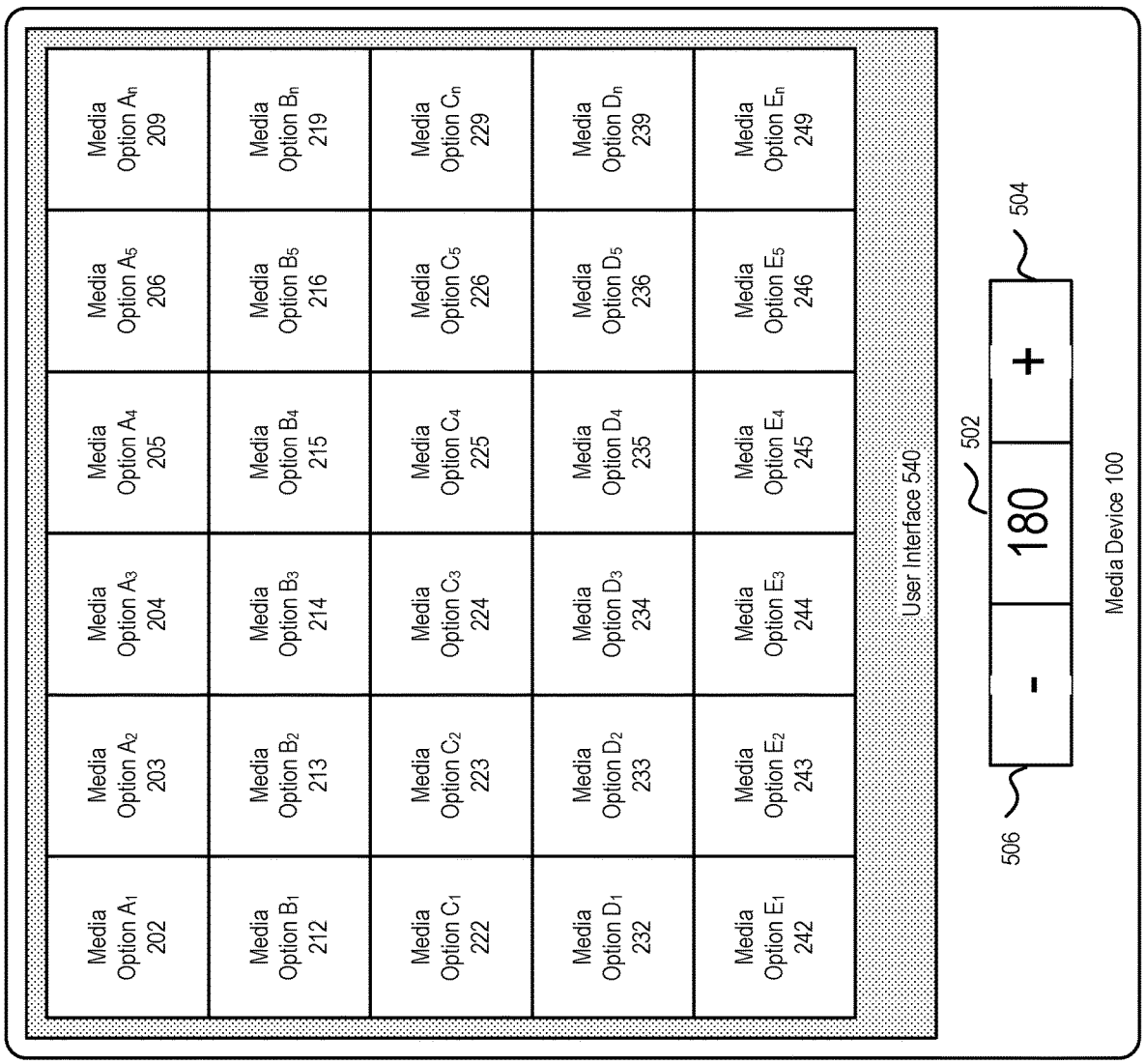
FIG. 17 illustrates the media device with another exemplary user interface which supports multi-track playback of media content, in accordance with an embodiment.

FIG. 17 illustrates the media-playback device 100 with another exemplary user interface 540 which supports multi-track playback of media content, in accordance with an embodiment. This user interface 540 is similar to the user interface 140 shown in FIG. 5, in that the user interface 540 provides a visual array of media options arranged as a two-dimensional grid, with rows and columns of media options visualized as tiles, here illustrated as $A_1$-$A_n$ through $E_1$-$E_n$ (202-249). Each of the media options is associated with one or more media content items that can be played on the device.

The user interface 540 also includes a tempo selection module including a current tempo indicator 502, an increase tempo selector 504, and a decrease tempo selector 506.

In this example, the current tempo indicator 502 provides an indication of the current tempo of one or more of the media options $A_1$-$A_n$ through $E_1$-$E_n$ (202-249) shown in the user interface 540. For example, by setting the current tempo indicator 502 to a desired tempo (e.g., 180), the user interface 540 is programmed to provide media options with a tempo of 180 (or a close approximation thereto).

The user interacts with the user interface 540 in a similar manner to the user interface 140 described above, in that the user can provide input as a user selection of a point or region on the user interface 540. The user interface 540 can be a touch-sensitive user interface, which recognizes input in the form of touch, for example the position of a user's finger or a stylus upon the user interface, to determine the selected point or region within the visual array of media options.

In one example, the current tempo indicator 502 of the tempo selection module provides a default or desired tempo on the current tempo indicator 502. For example, a cadence of 180 steps per minute is sometimes considered to be an optimal cadence. In such scenarios, the current tempo indicator 502 is programmed to default to a tempo of 180 beats, which generally corresponds to the cadence of 180. In other embodiments, the media-playback device 100 can be programmed to provide a different default tempo as set by the user.

In another example, the media-playback device 100 can be programmed to automatically set the tempo provided by the current tempo indicator 502 based upon one or more criteria. For example, the media-playback device 100 can be programmed to determine a current cadence of the user, as noted. This current cadence can be translated into a tempo, and that current tempo can be presented on the current tempo indicator 502.

For example, if the media-playback device 100 estimates that the user is running at a cadence of 170 steps per minute, the media-playback device 100 is programmed to show 170 in the current tempo indicator 502. By setting the current tempo indicator 502 to 170 beats, the media options $A_1$-$A_n$ through $E_1$-$E_n$ (202-249) (e.g., songs, etc.) shown in the user interface 540 match or approximate that tempo. The current tempo indicator 502 can be modified periodically (e.g., once per second, once every five seconds, once every ten seconds, etc.) to approximate a current cadence of the user.

In yet another embodiment, the user can use the increase tempo selector 504 and/or the decrease tempo selector 506 to change the tempo displayed in the current tempo indicator 502. For example, the user can select the increase tempo selector 504 one or more times to increase the tempo displayed by the current tempo indicator 502. The user may do so, for example, if the user wishes to increase his/her cadence. In doing so, the media options $A_1$-$A_n$ through $E_1$-$E_n$ (202-249) (e.g., songs, etc.) shown in the user interface 540 will change to media options matching or approximating the new desired tempo.

For example, when the current tempo indicator 502 indicates a tempo of 180, media options having that tempo are displayed in the user interface 540. If the user thereupon changes the current tempo indicator 502, using the increase tempo selector 504, to a tempo of 190 (e.g., if the user wishes to increase his/her cadence), then the user interface 540 is modified to show media options having or approximating the new tempo of 190. Similarly, the user can decrease the tempo by selecting the decrease tempo selector 506 one or more times.

Other options are possible. For example, in one embodiment, the user can select the current tempo indicator 502 to bring up a keypad that allows the user to directly input a desired tempo. In yet another example, the tempo can be increased and/or decreased at periodic intervals or at desired points throughout the user's activities to impact or assist the user to attain or maintain a desired cadence.

In the illustrated examples, the user interface 540 is populated with short, unencrypted samples 132 (e.g., 30 second snippets) of the media options, as provided by the server 102. This allows for the media options (e.g., songs, videos, etc.) to be provided efficiently by the server 102 in the manners describe above.

Figure 18:
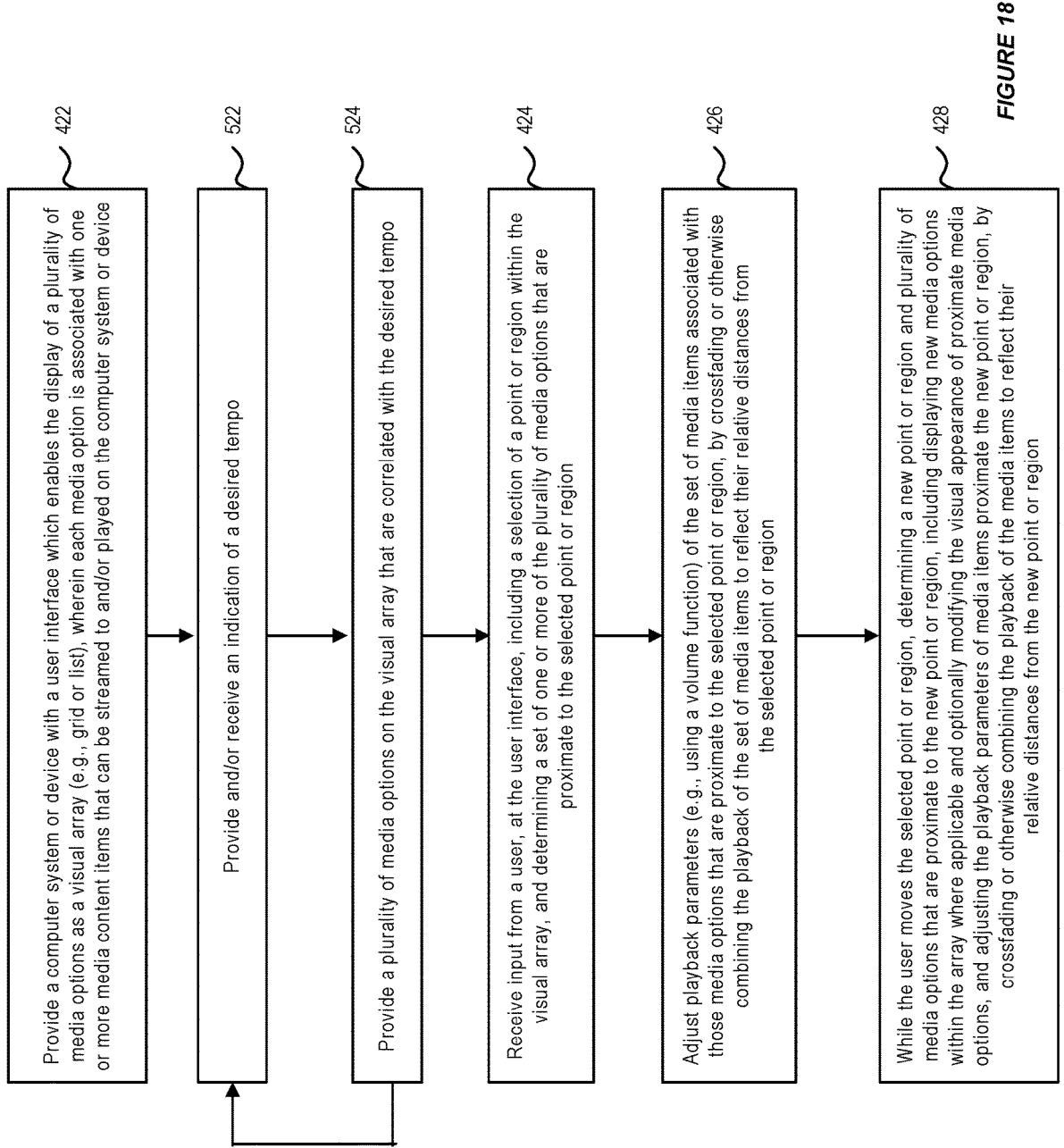
FIG. 18 is a flowchart of another method for multi-track playback of media content, in accordance with an embodiment.

Referring now to FIG. 18, a flowchart of an example method is shown for selecting a desired tempo and/or providing a plurality of media options at a tempo. This method is similar to that of FIG. 15, with the noted exceptions.

At step 422, a computer system or device is provided with a user interface which enables the display of a plurality of media options as a visual array (e.g., a grid or list), wherein each media option is associated with one or more media content items that can be streamed to and/or played on the computer system or device.

At step 522, a desired tempo is provided. As noted, this tempo is typically correlated with a cadence, and the tempo can be a preset tempo, a tempo that is correlated to a current cadence of the user, and/or a tempo selected by the user.

At step 524, a plurality of media options are provided that are correlated (e.g., are at or approximate) with the desired tempo are provided on the user interface.

In some examples, the media-playback device 100 sends a query to the server 102 to obtain populate the visual grid. This query can include, among other parameters, the desired tempo and a request that the returned samples have a certain runnability, as described in U.S. Patent Application Ser. No. 62/163,921, titled IDENTIFYING MEDIA CONTENT, filed on May 19, 2015, the entirety of which is hereby incorporated by reference. For example, the media stream service 120 can be programmed to provide snippets 132 of media content that meet a desired tempo and runnability score, as defined in the request from the media-playback device 100.

At step 424, an input is received from a user, at the user interface, including a selection of a point or region within the visual array, which can be used to determine a set of one or more of the plurality of media options that are proximate to the selected point or region.

At step 426, the playback parameters (e.g., the playback volume) of the set of media content items associated with those media options that are proximate to the selected point or region, are adjusted by crossfading or otherwise combining the playback of the set of media content items to reflect their relative distances from the selected point or region.

At step 428, while the user moves the selected point or region, a new point or region and plurality of media options that are proximate to the new point or region is determined, including displaying new or additional media options within the visual array where applicable and optionally modifying the visual appearance of proximate media options. The playback of media content items proximate the new point or region are again adjusted, by crossfading or otherwise combining their playback to reflect their relative distances from the new point or region.

The process can continue with the user continuing to move the selected point or region and the playback of proximate media content items continually adjusted, by crossfading or otherwise combining their playback.

In some examples, the device and/or the user can modify the desired tempo, so that a new tempo is provided at step 522, and a new plurality of media options is provided at step 524.

In certain embodiments, the beats of each preview of the media content are aligned as the user moved between the previews on the visual grid. In other words, the selected beat is maintained as the user selects among the media content. This can be important so that the desired tempo is maintained regardless of when the user moves between previews on the visual grid. In this example, the system modifies the transitions between previews as needed to maintain the desired or selected beat. Examples of technologies that can align beats between media content are provided in U.S. Patent Application Ser. No. 62/163,882, titled CADENCE-BASED SELECTION, PLAYBACK, AND TRANSITION BETWEEN SONG VERSIONS, filed on May 19, 2015, which is hereby incorporated by reference in its entirety.

Various methods can be used to select media content of a particular tempo that corresponds to a desired cadence. Examples of such methods are provided in U.S. Patent Application Ser. No. 62/163,927, titled SEARCH MEDIA CONTENT BASED UPON TEMPO, filed on May 19, 2015, which is hereby incorporated by reference in its entirety.

In one alternative embodiment, the user can select a media content of a desired tempo. For example, the user may have a particular song to which the user likes to run or otherwise engage in repetitive motion activities. Once the user selects this song, the song can be populated on the visual grid, and the system can be configured to (i) populate other songs with similar tempos on the grid, and/or (ii) identify the tempo of that song, such as by populating the tempo of the song in the current tempo indicator. This would allow the user to find other songs of a similar tempo for running.

There can be various advantages to allowing the user to automatically and/or manually select media content of a specific tempo. For example, as noted, the tempo of the media content can impact the user's cadence. So, selection of specific media content of a specific tempo can cause the user to maintain a given cadence and/or to increase or decrease a given cadence, as desired.

Further, presenting the media content on the visual grid as described herein has various advantages. For example, the user may utilize the system as the user is engaged in a particular activity, such as running. When running, it can be difficult to see and manipulate an interface. The visual grid described herein allows the user to easily slide the user's finger across the grid until a song of a desired tempo is located. This could be accomplished, for example, with the user focusing his or her visual attention on the specific media content in the grid. Instead, the selection could be accomplished through listening to the previews provided as the user slides her finger across the grid.

Embodiments of the present invention may be conveniently implemented using one or more conventional general purpose or specialized digital computer, computing device, machine, or microprocessor, including one or more processors, memory and/or computer readable storage media programmed according to the teachings of the present disclosure. Appropriate software coding can readily be prepared by skilled programmers based on the teachings of the present disclosure, as will be apparent to those skilled in the software art.

In some embodiments, the present invention includes a computer program product which is a non-transitory storage medium or computer readable medium (media) having instructions stored thereon/in which can be used to program a computer to perform any of the processes of the present invention. Examples of the storage medium can include, but is not limited to, any type of disk including floppy disks, optical discs, DVD, CD-ROMs, microdrive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data.

The foregoing description of embodiments of the present invention has been provided for the purposes of illustration and description. It is not intended to be exhaustive or to limit the invention to the precise forms disclosed. Many modifications and variations will be apparent to the practitioner skilled in the art.

For example, although the above examples generally describe the providing of music media content, such as songs, and the use of song cover art as a visualization to be used with the media options, the systems, methods and techniques described herein can be used with other forms of media content, including but not limited to video media content. Additionally, although the above examples generally describe the use of grid, list, or other tile-based visual arrays, with generally square, rectangular, or hexagonal tiles, the systems, methods and techniques can be used with other types of visual arrays, layouts, shapes of media options, visualization, and appearances.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalents.

What is claimed is:

1. A system for multi-track playback of media content, comprising:
   a media device, including a processor;
   a tempo logic, provided within the media device, configured to identify a cadence associated with a repetitive motion activity, and to provide a plurality of media content items associated with a tempo that corresponds to the cadence;
   a user interface, provided at the media device, configured to:

display a visual array of media options, wherein each of the media options is associated with one of the plurality of media content items provided by the tempo logic;

receive a first user input comprising a selection of a first region corresponding to a first media option in the visual array, the first media option associated with a first media content item from the plurality of media content items; and receive a second user input comprising a sliding movement of the selection from the first region to a second region corresponding to a second media option in the visual array, the second media option associated with a second media content item from the plurality of media content items; and a playback logic, provided within the media device, configured to initialize a playback of the first media content item upon the receipt of the first user input, and in response to a determination that a distance between a position of the second user input and a specified point of the second media option is less than a defined distance, cease the playback of the first media content item as a playback of the second media content item is initialized such that the playback of the first media content item and the playback of the second media content item do not overlap.

2. The system of claim 1, wherein the playback logic is further configured to adjust playback parameters for each of the first media content item and the second media content item, the adjusted playback parameters comprising at least a playback volume of each of the first media content item and the second media content item.

3. The system of claim 1, wherein the tempo logic is further configured to automatically modify the tempo based upon identified changes to the cadence.

4. The system of claim 1, wherein the tempo logic includes a tempo selection module configured to allow a user to manually adjust the tempo, the tempo selection module comprising an increase tempo selector that increases the selected tempo when selected and a decrease tempo selector that decreases the selected tempo when selected.

5. A method for multi-track playback of media content, comprising:

identifying a tempo associated with a cadence for a repetitive-motion activity;

providing a plurality of media content items associated with the tempo;

providing a user interface, at a media device, which displays a visual array of media options, wherein each media option is associated with one of the plurality of media content items that can be played on the media device;

receiving, through the user interface, a user input comprising a selection of a first region corresponding to a first media option in the visual array, the first media option associated with a first media content item from the plurality of media content items;

initializing playback of the first media content item on the media device;

receiving, through the user interface, a continuation of the user input comprising a movement of the selection from the first region to a second region corresponding to a second media option in the visual array, the second media option associated with a second media content item from the plurality of media content items; and in response to a determination that a distance between a position of the continuation of the user input and a specified point of the second media option is less than a defined distance, cease the playback of the first media content item as initializing a playback of the second media content item is initialized on the media device such that the playback of the first media content item and the playback of the second media content item do not overlap.

6. The method of claim 5, wherein identifying the tempo further comprises:

automatically selecting the tempo based upon an estimated cadence of a user; and automatically modifying the tempo based upon changes in the estimated cadence of the user.

7. The method of claim 5, further comprising:

one of increasing and decreasing the tempo based on manual adjustments to the tempo received from a user.

8. The method of claim 5, further comprising:

populating the visual array of media options with snippets of the plurality of media content items.

9. The method of claim 8, further comprising:

selecting each of the snippets based upon the tempo and a runnability score.

10. The method of claim 8, further comprising:

in response to the selection remaining in the first region for a period of time, appending a remainder of the first media content item to a snippet of the first media content item.

11. A non-transitory computer readable storage medium, including instructions stored thereon which when read and executed by one or more computers cause the one or more computers to perform steps comprising:

receiving, by a media device, a selection of a tempo associated with a cadence for a repetitive-motion activity;

selecting, by the media device, a plurality of media content items that can be played on the media device, wherein the plurality of selected media content items are associated with the tempo;

providing a user interface comprising a plurality of media options in a visual array, wherein each of the plurality of media options is associated with one of the plurality of media content items;

receiving, through the user interface, a user input comprising a selection of a first region corresponding to a first media option in the visual array, the first media option associated with a first media content item from the plurality of media content items;

initializing, by the media device, playback of the first media content item;

receiving, through the user interface, a continuation of the user input comprising a movement of the selection from the first region to a second region corresponding to a second media option in the visual array, the second media option associated with a second media content item from the plurality of media content items; and in response to a determination that a distance between a position of the continuation of the user input and a specified point of the second media option is less than a defined distance, ceasing, by the media device, the playback of the first media content item as initializing a playback of the second media content item is initialized such that the playback of the first media content item and the playback of the second media content item do not overlap.

12. The non-transitory computer readable storage medium of claim 11, further comprising:

adjusting playback parameters for each of the first media content item and the second media content item, the adjusted playback parameters comprising at least a playback volume of each of the first media content item and the second media content item.

\* \* \* \* \*

UNITED STATES PATENT AND TRADEMARK OFFICE
CERTIFICATE OF CORRECTION

PATENT NO. : 10,671,155 B2  
APPLICATION NO. : 16/279957  
DATED : June 2, 2020  
INVENTOR(S) : Dariusz Dziuk Page 1 of 1

It is certified that error appears in the above-identified patent and that said Letters Patent is hereby corrected as shown below:

In the Claims

Column 20, Line 3, Claim 5: "content item as initializing a playback" should read --content item as a playback--

Column 20, Line 61, Claim 11: "content item as initializing" should read --content item as--

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*